United States Patent
Miedl et al.

(10) Patent No.: US 10,766,030 B2
(45) Date of Patent: Sep. 8, 2020

(54) METHOD AND APPARATUS FOR THE DETECTION OF BACTERIA

(71) Applicants: SINAMIRA AG, Grünwald (DE); FRIEDRICH-ALEXANDER-UNIVERSITÄT ERLANGEN-NÜRNBERG, Erlangen (DE)

(72) Inventors: Walter Miedl, Appenzell (CH); Oliver Friedrich, Nürnberg (DE); Daniel Gilbert, Nürnberg (DE)

(73) Assignees: SINAMIRA AG, Grümwald (DE); FRIEDRICH-ALEXANDER-UNIVERSITÄT ERLANGEN-NÜRNBERG, Erlangen (DE)

( * ) Notice: Subject to any disclaimer, the term of this patent is extended or adjusted under 35 U.S.C. 154(b) by 12 days.

(21) Appl. No.: 15/777,662

(22) PCT Filed: Nov. 18, 2016

(86) PCT No.: PCT/EP2016/001925
§ 371 (c)(1),
(2) Date: May 19, 2018

(87) PCT Pub. No.: WO2017/084754
PCT Pub. Date: May 26, 2017

(65) Prior Publication Data
US 2018/0339293 A1  Nov. 29, 2018

(30) Foreign Application Priority Data

Nov. 20, 2015 (EP) ..................... 15003307

(51) Int. Cl.
*C12Q 1/04* (2006.01)
*B01L 3/00* (2006.01)
*G01N 33/569* (2006.01)

(52) U.S. Cl.
CPC ......... *B01L 3/502715* (2013.01); *B01L 3/502* (2013.01); *B01L 3/545* (2013.01); *C12Q 1/04* (2013.01); *G01N 33/56911* (2013.01); *B01L 2300/021* (2013.01); *B01L 2300/022* (2013.01); *B01L 2300/0654* (2013.01); *B01L 2300/0681* (2013.01); *B01L 2300/0816* (2013.01); *B01L 2300/0864* (2013.01); *Y02A 50/52* (2018.01); *Y02A 50/57* (2018.01); *Y02A 50/59* (2018.01)

(58) Field of Classification Search
None
See application file for complete search history.

(56) References Cited

U.S. PATENT DOCUMENTS

2001/0006783 A1   7/2001   Nogami

FOREIGN PATENT DOCUMENTS

WO   2006105504 A1   10/2006

OTHER PUBLICATIONS

English Translation of the International Search Report (only) issued in PCT/EP2016/001925, dated Jan. 23, 2017.
Mosier-Boss, P.A., et al.; "Use of Fluorescently Labeled Phage in the Detection and Identification of Bacterial Species"; Applied Spectroscopy; vol. 57, No. 9; pp. 1138-1144; (2003).

*Primary Examiner* — Oluwatosin A Ogunbiyi
(74) *Attorney, Agent, or Firm* — Insigne LLP

(57) ABSTRACT

The present invention relates to a fast, simple and very sensitive method for the detection of bacteria, comprising the steps of providing one or more suspensions each comprising at least one species of labeled test bacteriophages which specifically bind to a bacterial species to be detected; adding a sample to be tested for the presence of at least one bacterial species to be detected to the one or more suspensions; filtering the reaction mixture; detecting bacteria-bacteriophages-complexes on the surface of the filter in the retentate, provided that at least one bacterial species to be detected is present, wherein the complexes consist of bacteria of the at least one bacterial species to be detected and test bacteriophages of the at least one species of test bacteriophages bound thereto; detecting unbound test bacteriophages in the filtrate; processor-aided processing of received detection signals and output of detection results.

22 Claims, 13 Drawing Sheets

Excitation spectrum　　　　　Emission spectrum

METHOD AND APPARATUS FOR THE DETECTION OF BACTERIA

Figure 1:
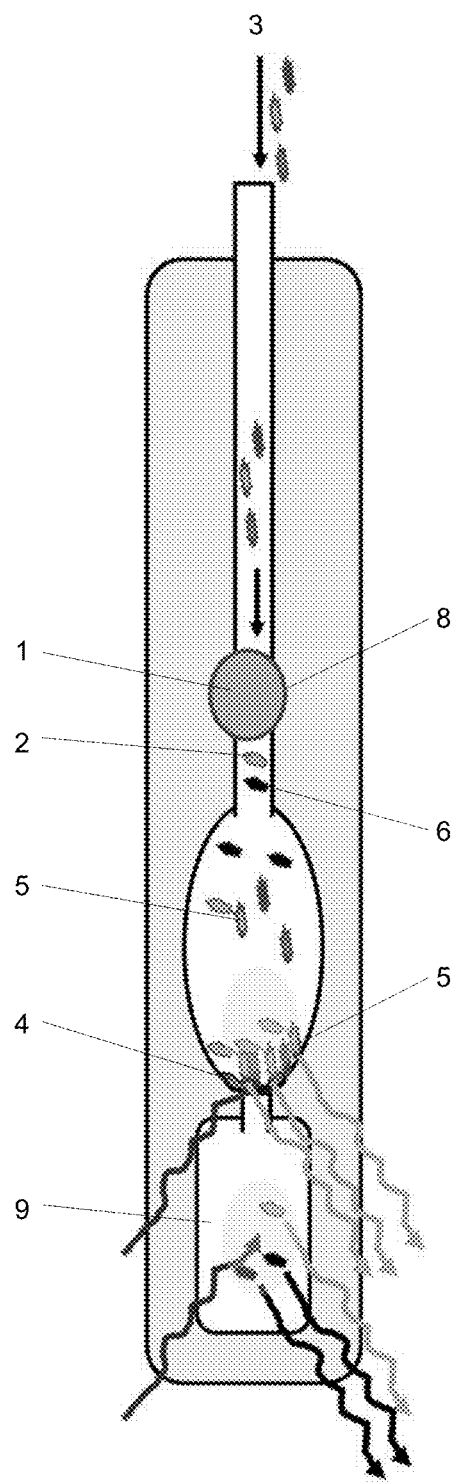

This present invention relates to a method for the detection of bacteria, in particular an accelerated and highly sensitive method for the detection of bacterial pathogens, which is based on the formation of specific bacteria-bacteriophages-complexes. In addition, a reaction vessel and a measuring device for carrying out the inventive method are disclosed.

Bacteria are often characterized as pathogens of serious diseases. In particular, multi-resistant bacterial strains, also known as "hospital pathogens", are responsible for a large number of bacterial infections in hospitals. Especially in view of the demographic change and the possibilities of modern intensive care medicine, an increasing number of elderly patients who are particularly susceptible to bacterial infections are found in intensive care units. One of the central building blocks of intensive care therapy is microbiological diagnostics. A quick and correct identification of the pathogens of an infection not only significantly influences the mortality of patients, but also enables the use of germ specific antibiotics, so that an inflationary use of broad-spectrum antibiotics and the associated selection of multi-resistant bacterial strains can be avoided. However, the hitherto existing procedures are usually time-consuming and also cost-intensive.

For example, blood cultures have been one of the main pillars in the diagnosis of blood flow infections to date. Thereby, incubation takes place in culture flasks under aerobic and anaerobic conditions. In addition to blood, sterile fluids such as punctates or liquor samples are suitable for this purpose. In general, about 3-4 culture flasks each containing 10 ml whole blood are taken for diagnosis at room temperature. The blood culture flasks are incubated in a semi-automatic system in which the increasing growth of bacteria is measured by the increasing production of $CO_2$ or by an increase of the bottle pressure. The routine incubation is 48-72 hours in most cases. Thereby, slow-growing bacteria, which can require incubation of 5 to 21 days and are, therefor, easily overlooked in routine procedures, pose particular problems. Likewise, special culture media or colouring processes complicate and delay a sufficient and quick diagnosis. If a blood culture flask is positively detected, it is selected from the system. A sample is taken from this bottle and aerobic and anaerobic sub-cultures are again prepared on different culture media. After a further eight hours, a rough determination of the resistance with accompanying antibiotic testing can be carried out.

Faster pathogen identification is achieved directly from the positive blood culture flask within 1-2 hours using latex agglutination for the detection of antigens of *Streptococcus pneumoniae, Streptococcus agalactiae, Haemophilus influenzae, Neisseria meningitis, E. coli* and *Salmonella typhi*. Methods for the detection of nucleic acids, such as DNA hybridization, fluorescence in situ hybridization (FISH) and specific nucleic acid amplification techniques (NAT), have been used for the diagnostics of bacteremia and sepsis in recent times, but are only available in very few laboratories. Thereby, the pathogen can be determined within 1-3 hours from a positive blood culture flask. In addition, some clinical laboratories have been upgraded in recent years with MALDI-TOF (matrix-assisted laser desorption/ionisation time of flight) mass spectrometers, which allow the identification of bacteria within just a few minutes. However, the modern detection methods described above still require a positively detected blood culture flask. Therefore, the detection of bacterial pathogens using a positive blood culture can usually succeed only within a time window of from 24 to 36 hours after taking the sample.

In some cases, PCR diagnostic methods enable the detection of bacteria from blood samples within 4-6 hours after the taking of the blood samples of collection without the intermediate step of incubation of a blood culture, e.g. for *Staphylococcus aureus*. The most modern methods are multiplex amplification methods, which can detect the most common pathogens. These include LightCycler, SeptiFast and SepsiTest. However, these tests are quite susceptible to contaminations, which give false or false positive results. Another disadvantage of these methods is the amount of work and the cost structure, as PCR diagnostics requires not only the material but also appropriate specialist personnel and a suitable infrastructure.

Furthermore, it should be noted that in 2-3% of all cases, a positively detected blood culture also originates from a contamination of the sample or processing errors after the sampling. The consequences are incorrect antibiotic therapies with unnecessary and sometimes considerable costs, which is why a rapid, easy-to-use and highly sensitive method for the detection of bacterial pathogens would be desirable.

With regard to the requirements of high sensitivity and specificity, bacteriophages (phages for short) offer a promising starting point. Bacteriophages are viruses that specifically target bacterial cells, recognise them via surface receptor structures, bind them in a key-lock-like manner and use the genetic and enzymatic equipment of the bacteria for their own reproduction in the subsequent steps. The infected bacterial cells lyse and release numerous new phages. This biological process chain continues until all host bacterial cells accessible to the free phage have been removed. Phages almost always affect only strains within one bacterial species, i.e. they are highly specific for a certain bacterial species. Since many bacterial species can be found ubiquitously in numerous habitats, according to a biological principle, it can be expected that their complementary phages are also found therein. Globally, the number of phages estimated by experts exceeds that of bacteria tenfold (C. Rohde & J. Sikorski: Bakteriophagen—Vielfalt, Anwendung and ihre Bedeutung für die Wissenschaft vom Leben. *Naturwiss. Rundschau* (2011), 64, 5-14). The desired bacteriophages can often be extracted from all conceivable aqueous habitats by simple sampling and subsequent screening against the target bacteria.

Due to their enormous host specificity and lytic properties, phages are already used in a manifold manner in clinical research and analysis, e.g. in phage therapy against bacterial infections. Furthermore, Thanki, Malik, Clokie describe the development of a bioluminescent reporter phage for the identification of *Clostridium difficile*, in which the gene cassettes luxA and LuxB encoding the enzyme luciferase, are cloned into a plasmid for conjugation into a *Clostridium difficile*-specific phage and for homologous insertion into the phage genome (A. Thanki, D. Malik, M. Clokie, The Development of a Reporter Phage for the Identification of *Clostridium difficile, Bacteriophages* (2015), Abstract, 25). The scientific publication of Mosier-Boss et al. further describes the specific detection of *Salmonella typhimurium* LT2 using fluorescence-labelled P22 phages. The label of the phage is completely limited to the DNA of the phage (10 min incubation of P22 with SYBR gold), which is injected into the host bacterium upon infection. The detection of specific *Salmonella typhimurium*-P22-phages complexes is carried out after their isolation by fluorescence microscopy.

(P. A. Mosier-Boss et al.' Use of Fluorescently Labeled Phage in the Detection and Identification of Bacterial Species, *Applied Spectroscopy* (2003), 57, 1138-1144).

Simple and reliable detection of bacteria is also important in the food industry and in drinking water supply. Legionella strains can proliferate in drinking water at temperatures between 20 and 45° C., so that regular testing of drinking water is required and is also legally stipulated in many countries. For instance, the German drinking water regulation stipulates regular testing for Legionella. It is to be expected that the legal provisions will be further tightened. Institutes and authorities, e.g. drinking water laboratories or health authorities, are therefore anxious to carry out a fast, simple, sensitive and safe detection of bacteria of Legionella strains. This is currently lacking and an improvement is desirable.

On the other hand, food-borne bacterial food intoxications and food-toxin-infections are a global problem and cause massive economic damage. The long time period until a reliable detection of the pathogens is obtained means a considerable economic loss, as either the storage time of the products until resale is extended or the corresponding food can even be recalled. A quicker and safer detection method can significantly contribute to food safety and minimization of economic losses. Dreaded pathogens in the food sector include *Cronobacter* spp, *Salmonella* spp, *Shigella* spp, *Escherichia coli, Yersinia enterocolitica, Vibrio* spp, *Aeromonas* spp, *Plesiomonas* spp, *Listeria monocytogenes, Campylobacter jejuni*, or *Bacillus cereus*. A rapid exclusion or detection of pathogens in foods is therefore essential for their approval.

Other areas where rapid and simple detection of bacteria is desirable include the agricultural industry, veterinary medicine, military applications or disaster control.

In view of the disadvantages of the clinical methods for the detection of bacteria of the state-of-the-art, particularly with regard to expenditure of time, complexity and cost intensity, there is a need for a new, faster and more specific diagnostics is needed for a timely and selective detection of bacteria, be it for clinical, human medicinal or veterinary, agricultural or military applications, or for drinking water analysis, to name but a few specific applications. Therefore, it is the object of the present invention to provide an improved method for the detection of bacteria detection that provides a quicker and more reliable identification of bacterial pathogens, a simplified handling and a high sensitivity at lower cost. Likewise, a reaction vessel and a measuring device for carrying out the inventive method are provided.

The inventive solution to the above-mentioned object is based on the evolutionarily conserved, highly specific interaction between bacteria and bacteriophages.

Thus, the present invention discloses method for the detection of bacteria comprising the steps of
A) provision of one or more suspensions each comprising at least one species of labelled test bacteriophages which specifically bind to a bacterial species to be detected;
B) addition of a sample to be tested for the presence of at least one bacterial species to be detected to the one or more suspensions;
C) filtration of the resulting reaction mixture;
D) detection of bacteria-bacteriophages-complexes in the retentate, provided that at least one bacterial species to be detected is present, wherein the complexes consist of bacteria of the at least one bacterial species to be detected and test bacteriophages of the at least one species of test bacteriophages bound thereto;

E) detection of unbound test bacteriophages in the filtrate;
F) processor-aided processing of received signals generated by the detection in steps D) and E) and output of detection results to a user.

Furthermore, the present invention refers to a reaction vessel for carrying out the inventive method for the detection of bacteria, comprising
at least two compartments separated from each other by a filter, wherein one compartment is a phage reservoir containing a suspension which comprises at least one species of labeled test bacteriophages that specifically bind to a bacterial species to be detected, and one compartment is a collection reservoir for receiving the filtrate after the addition of a sample to the suspension and filtration through the filter;
a means for identifying the reaction vessel; and
at least two measurement windows, wherein one measurement window is arranged in the region of the filter surface facing the phage reservoir, and one measuring window is arranged in the region of the collection reservoir.

Moreover, the present invention concerns a cartridge, comprising two or more reaction vessels according to the invention, which are arranged parallel and/or in series to each other,
wherein each parallel reaction vessel contains different species of labeled test bacteriophages in the suspension of the phage reservoir, each specifically binding to different bacterial species to be detected.

In addition, the present invention relates to a measuring device for carrying out the inventive method for the detection of bacteria, comprising
a slot into which a reaction vessel according to the invention or a cartridge according to the invention is inserted;
at least two detection optics, each of which is arranged in the region of the measuring windows of the inserted reaction vessel or cartridge, wherein the detection optics each comprise a lens system for focusing light emitted by the label of the bacteriophages onto at least one sensor, the at least one sensor detecting the emitted light;
a processor which is connected to the at least one sensor of the detection optics, respectively, and which processes the received detection signals; and
an output unit connected to the processor, which outputs the detection results to a user.

On the one hand, the advantageous effect of the present invention lies in the quick and highly sensitive identification of bacterial pathogens. Thus, no blood culture is necessary for the inventive method Rather, a sample that is to be tested for the presence of a specific bacterial species can be used immediately after sampling. Therefore, bacteria can be detected ideally in less than 1 hour without the need to transport and store the sample. This allows a faster and more germ specific application of antibiotics, thus avoiding a prophylactic use of broad-spectrum antibiotics. In addition, by means of the inventive method, bacteria can be detected at concentrations of less than 100 bacteria per milliliter. On the other hand, the present method is characterized by the immediate use of the sample after its removal and ease of handling, making it less susceptible to processing errors. Furthermore, carrying out the method using the inventive reaction vessel and the inventive measuring instrument does not require proven specialist personnel or a special infrastructure, which considerably reduces costs.

FIGURES

FIG. 1: Schematic representation of a preferred embodiment of the inventive method for the detection of bacteria FIG. 2: Schematic representation of another preferred embodiment of the inventive method for the detection of bacteria FIG. 3 A: Schematic representation of a preferred embodiment of the inventive reaction vessel for the detection of bacteria FIG. 3 B: Theoretical course of a time-resolved measurement of the fluorescence in a preferred embodiment of the inventive method using the inventive reaction vessel of FIG. 3 A.

Figure 4:
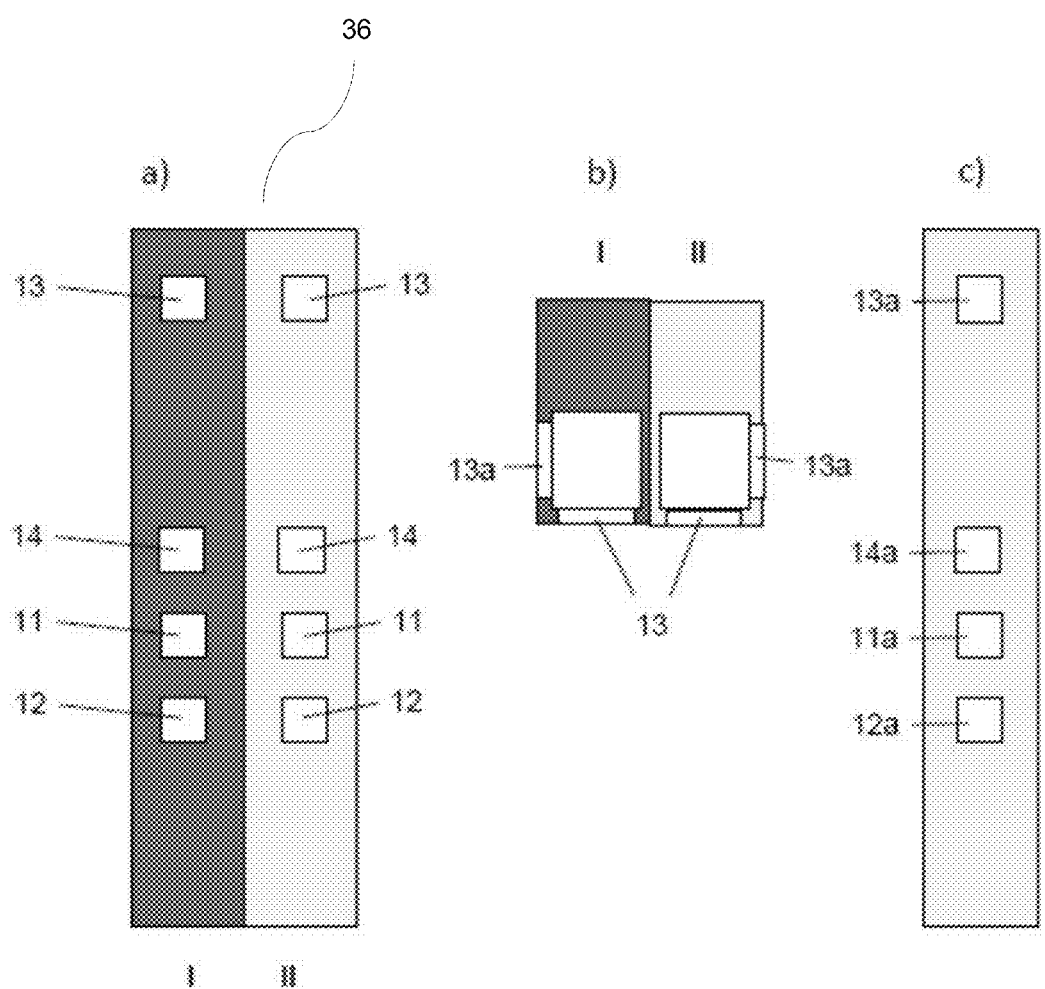
Figure 4:
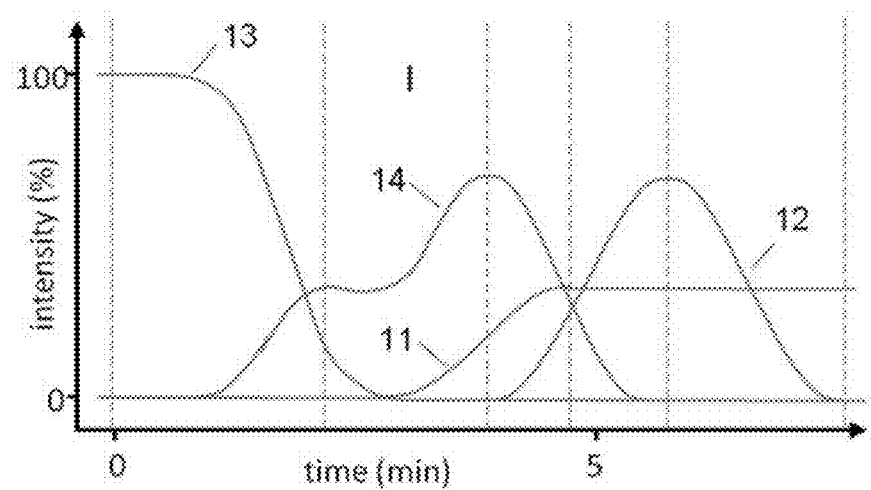
Figure 4:
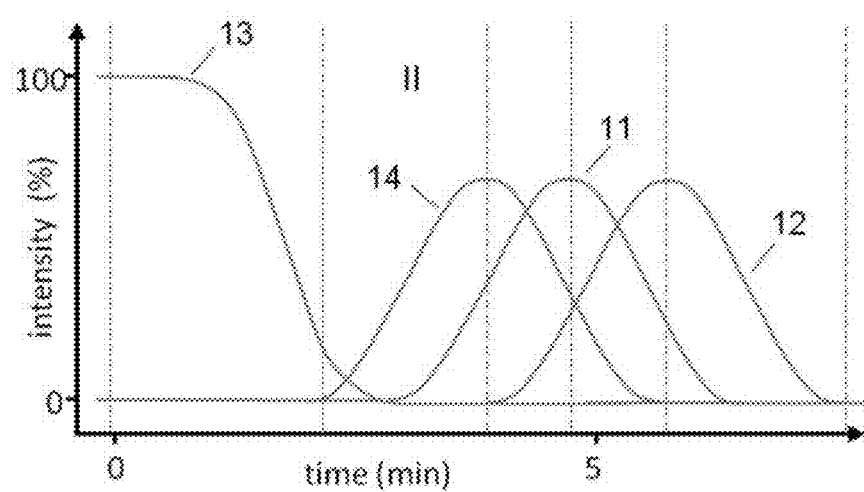

FIG. 4 A: Schematic representation of a preferred embodiment of the inventive cartridge for the detection of bacteria, a) front view, b) top view and c) side view.

FIG. 4 B: Theoretical courses of time-resolved measurements of the fluorescence in a preferred embodiment of the inventive method using the inventive cartridge of FIG. 4 A.

Figure 5:
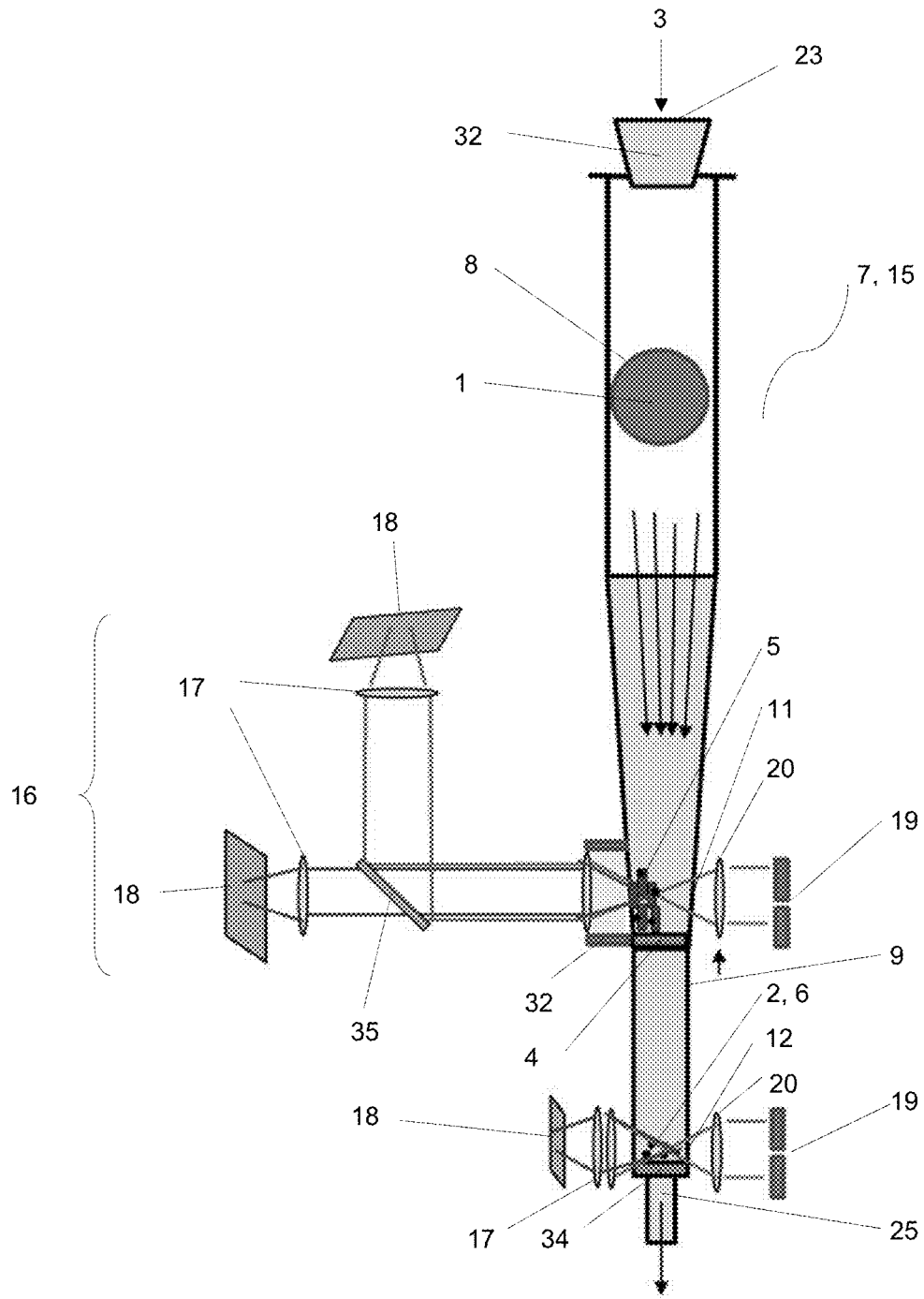

FIG. 5: Schematic representation of the assembly of the inventive reaction vessel and measuring device in one embodiment.

Figure 6:
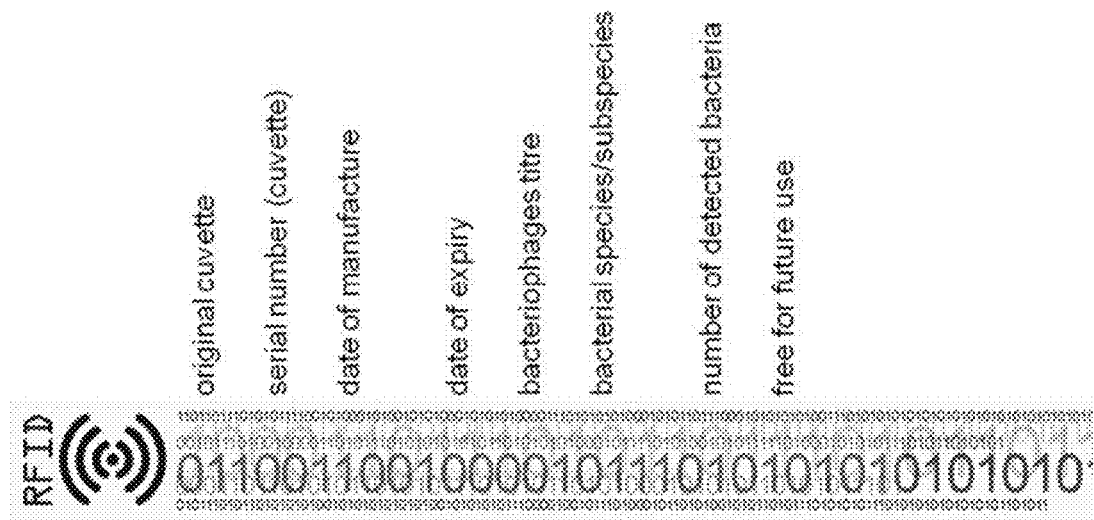

FIG. 6: RFID chip as a means for the identification of the inventive reaction vessel.

Figure 7:
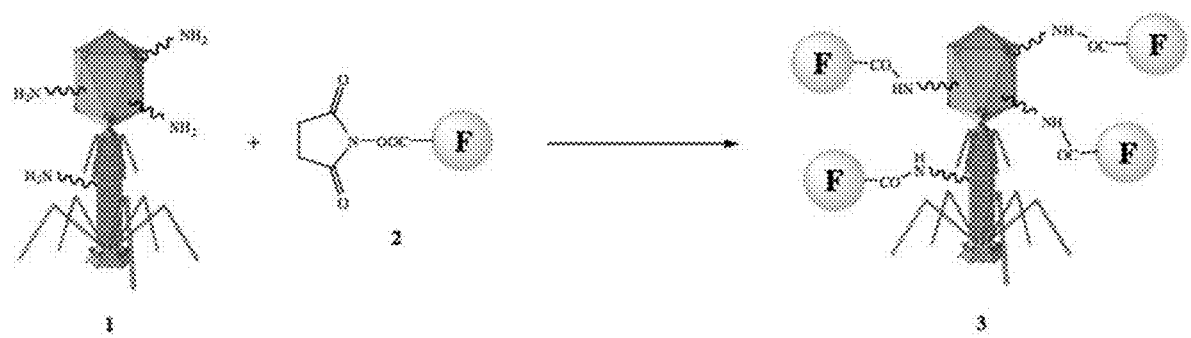

FIG. 7: Labelling of a TB54 bacteriophage with fluoresceine-NHS esters.

Figure 8:
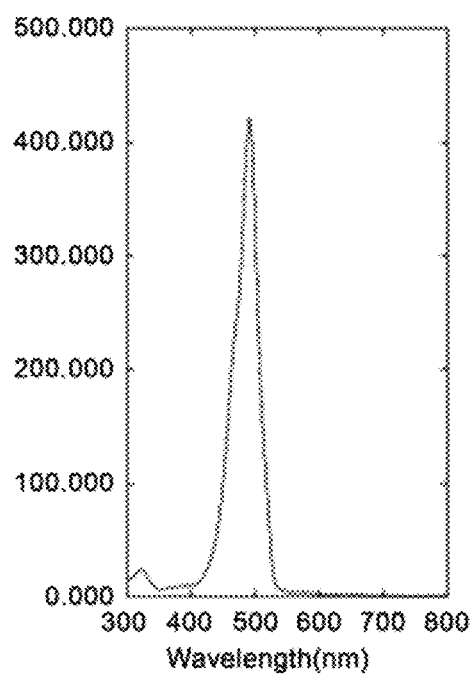
Figure 8:
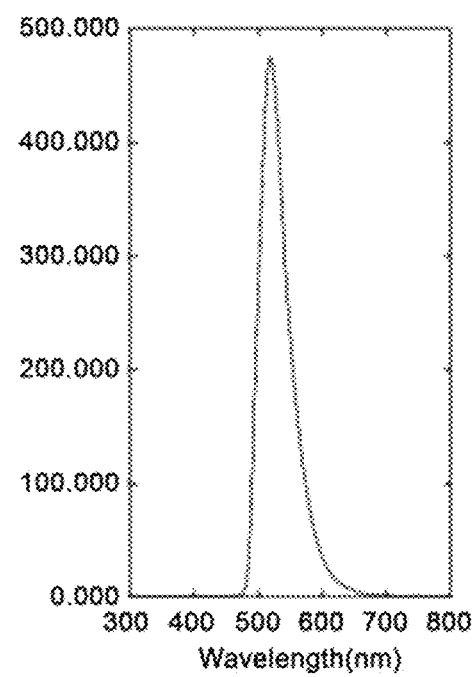

FIG. 8: Excitation and emission spectrum of fluoresceine-labelled TB54 bacteriophages.

Figure 9:
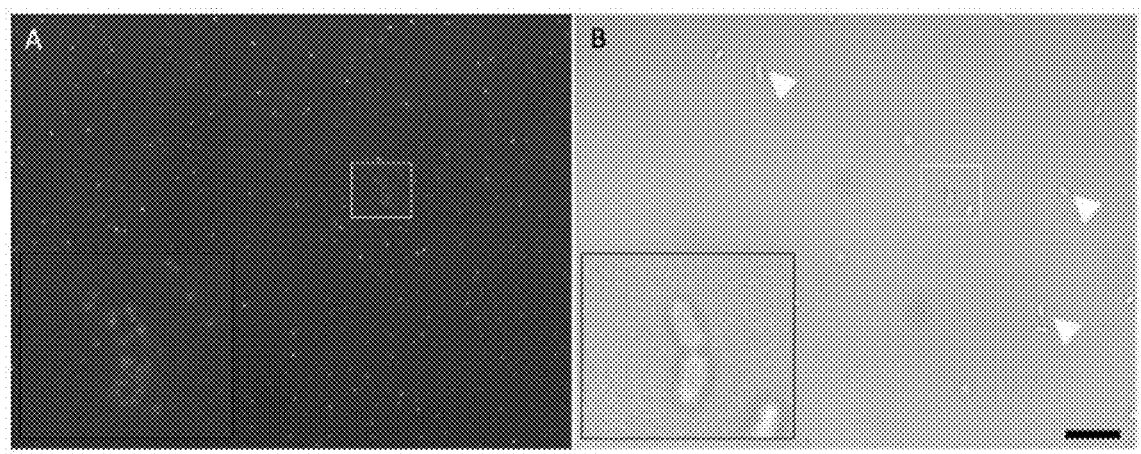

FIG. 9 A: Fluorescence microscope image of the bacteria-bacteriophages interaction.

FIG. 9 B: Brightfield image of the bacteria-bacteriophages interaction.

Figure 10:
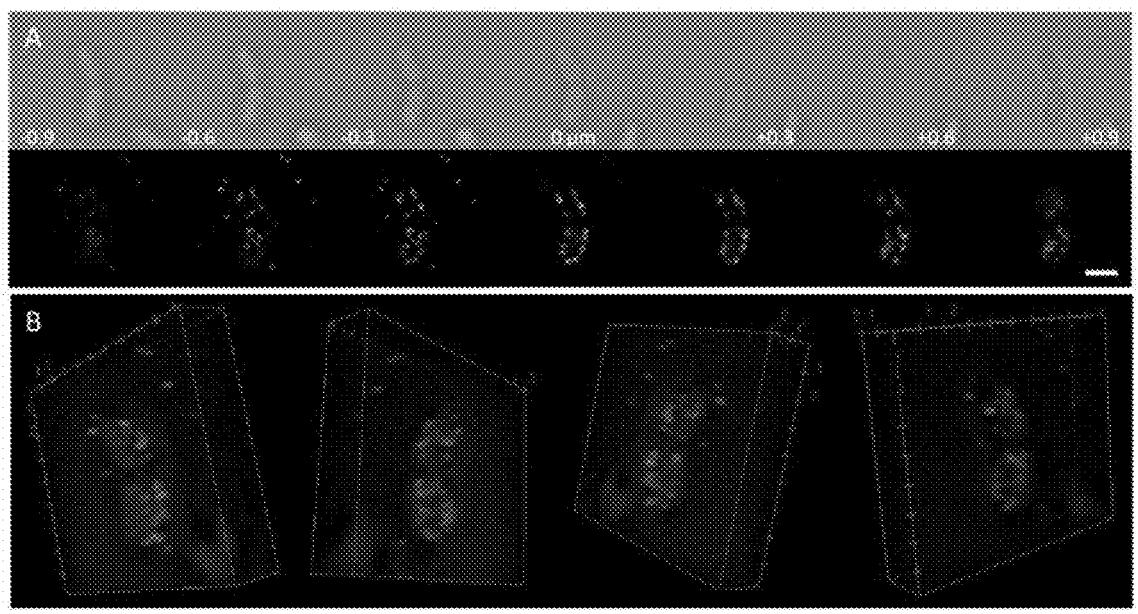

FIG. 10 A: Optical sectional images of *Escherichia coli* bacteria infected with fluoresceine-labelled TB54 bacteriophages in transmitted light and in fluorescence microscope representation.

FIG. 10 B: Three-dimensional reconstructions of *Escherichia coli* bacteria infected with fluoresceine-labelled TB54 bacteriophages.

Figure 11:
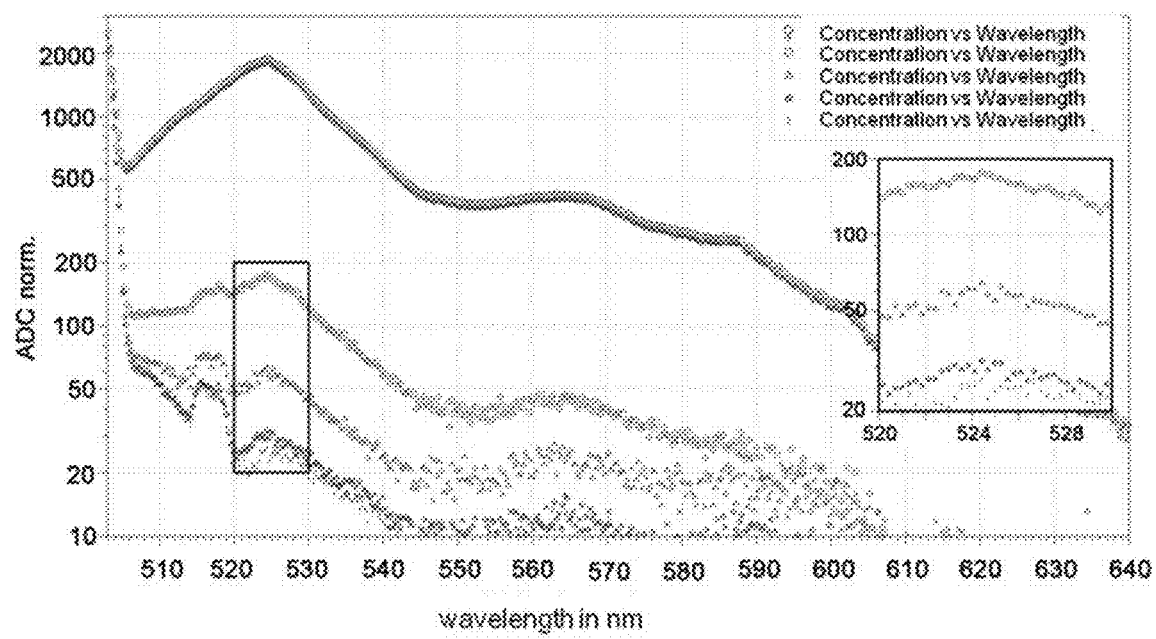
Figure 11:
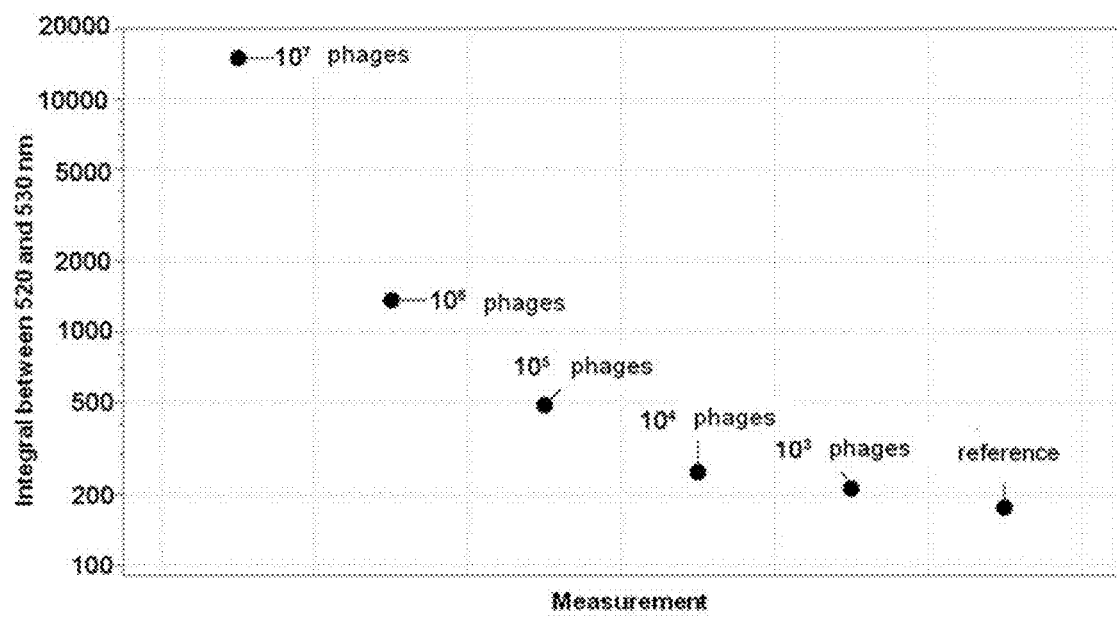

FIG. 11 A: Fluorescence spectra of fluoresceine-labelled TB54 bacteriophages at different concentrations of bacteriophages.

FIG. 11 B: Representation of the integrals between 520 and 530 nm of the fluorescence spectra of FIG. 10 A at different concentrations of bacteriophages.

Figure 12:
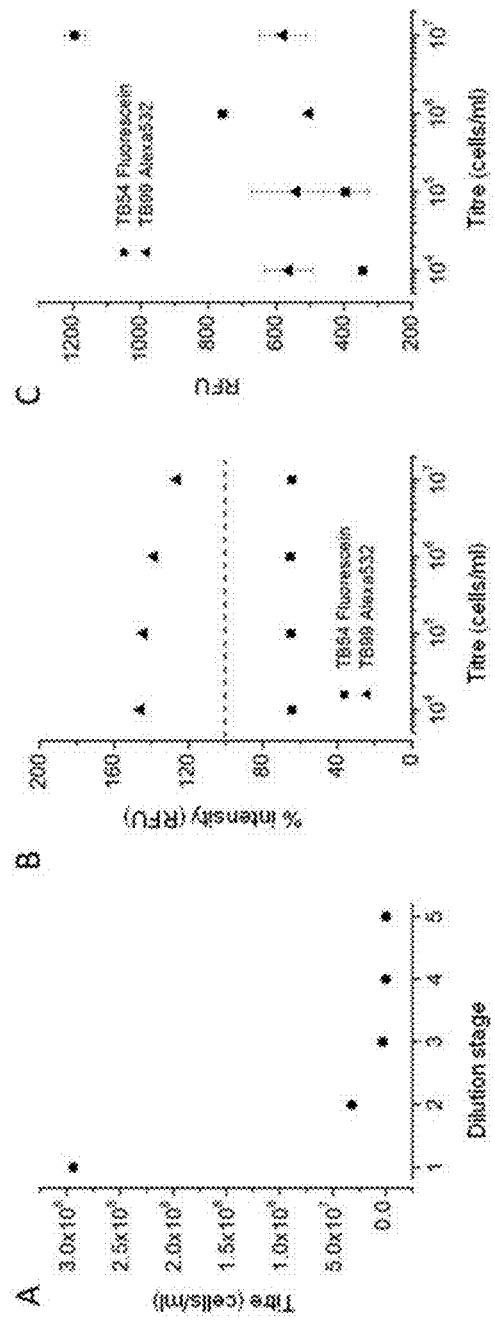

FIG. 12 A-C: Measurement of the optical density of a serially diluted bacterial suspension, representation of the detected fluorescence signals of *E. coli* C600-TB54 phages complexes on the filter surface in the retentate and representation of the detected fluorescence signals of unbound TB54 phages in the filtrate, each at different concentrations of the bacteria.

The method according to the invention comprises in step A) the provision of one or more suspensions, each of which comprises at least one species of labelled test bacteriophages, which specifically bind to a bacterial species to be detected. Preferably, the label is characteristic for the respective species of labelled test bacteriophages. This means that the labels that are coupled to different species of test bacteriophages are disjunct. Alternatively, the labels may also be partially overlapping, whereby the signals of the individual labels and of the different species of test bacteriophages, respectively, can be spectrally segregated by means of a spectroscopic analysis method and, thus, can be clearly assigned. In this case, overlapping labels may also be detected sequentially.

Preferably, the volume of the suspension is between 0.5 and 5.0 ml.

The concentration of bacteriophages in the suspension, also called phage titre, is preferably $10^3$-$10^{12}$ pfu/ml (pfu="plaque forming unit"), further preferably $10^4$-$10^{10}$ pfu/ml. Most preferred is a phage titre in the suspension of $10^5$-$10^7$ pfu/ml.

Depending on the bacterial species to be detected, a species of test bacteriophages, which specifically binds to this bacterial species, i.e. specifically infects this bacterial species, is selected for the preparation of the suspension. Due to the evolutionary conserved, enormous host specificity of the bacteriophages, it is even possible to specifically detect individual strains within a bacterial species. In this case, a species of test bacteriophages is selected for the preparation of the suspension, which specifically binds to a specific strain within a bacterial species. Thereby, binding of the selected species of test bacteriophages to a bacterial species other than the bacterial species to be detected or to a strain other than the strain to be detected is almost impossible. As a result, the possibility of obtaining false-positive detection by the inventive process is minimal and the result of the inventive detection method is extremely reliable. When providing several suspensions, different species of test bacteriophages, which each specifically bind to different bacterial species to be detected, may be selected accordingly so that each suspension contains one specific species of test bacteriophages. This makes it possible to detect several bacterial species within one sample. In order to be able to detect the test bacteriophages of the at least one species and the resulting bacteria-bacteriophages-complexes in the further procedure, the test bacteriophages carry a label. Preferably the label is characteristic for the respective species of test bacteriophages, i.e. all test bacteriophages of one species carry the same label, which is distinguishable from the labels of other species.

For preparing the suspension, the labelled test bacteriophages of the respective at least one species are preferably suspended in water or in a suitable buffer solution or other aqueous solution. Suitable buffer solutions are preferably 0.01-0.3 M phosphate buffer, pH 6.5-9.5; 0.01-0.3 M carbonate buffer, pH 6.5-9.5; phosphate-buffered saline (PBS) or mixtures thereof. Further preferred, the water and the suitable buffer solutions contain $MgCl_2$, $MgSO_4$ and/or $CaCl_2$. The concentration of $MgCl_2$, $MgSO_4$ and $CaCl_2$ preferably amounts to 1 to 15 mM each.

In step B) of the inventive method, a sample to be tested for the presence of at least one bacterial species to be detected is added to the one suspension or to the more suspensions. Preferably, the sample consists of a human or animal body fluid, such as blood, urine, saliva or another body fluid, a swab taken from a human or animal, water from a drinking water system or of food or food ingredients prepared in aqueous solution. After sampling, the sample may be added directly to the suspension or to the suspensions without further pre-treatment. Food or food ingredients are put into aqueous solution. This significantly reduces the time required for detection of bacteria and minimizes the risk of contamination during transport and/or storage. Furthermore, the inventive method also allows the detection of bacteria from a sample originating from a prepared bacterial culture.

Prior to the addition, the sample is preferably filtered through a coarse filter having a pore size of 0.5-10.0 µm in order to remove any contamination by particles (>0.5 µm) so that possible clogging of the filter in the subsequent step C) can be avoided. Alternatively, a multi-stage coarse filter having decreasing pore sizes of 0.5-10 µm may also be used.

The volume of the sample is preferably 0.05-2.5 ml, further preferably 0.1-2.0 ml and most preferably 0.5-2.0 ml. Combinations of said volume ranges are also possible.

Preferably, the sample is mixed with the suspension in a step G) following step B) and the resulting reaction mixture is incubated. The mixing is preferably carried out by repeated swivelling or moderate stirring. The resulting reaction mixture is preferably incubated for 2-30 min, further preferably for 5-15 min, and even more preferably for 5-10 min. The temperature during incubation is preferably 4-60° C., further preferably 10-30° C. Incubation of the reaction mixture at room temperature (RT, 20-25° C.) is most preferred. Provided that at least one bacterial species to be detected is present, the mixing and incubation is supposed to ensure that each bacterium to be detected is bound or infected by the labeled test bacteriophages of the respective at least one species before the subsequent filtration in step C).

Preferably, a filter having a pore size of 0.1-0.5 μm is used for the filtration of the reaction mixture in step C). The pore size of the filter used is further preferably 0.2-0.5 μm while a pore size of 0.3-0.5 μm is particularly preferred and a pore size of 0.2-0.4 μm is most preferred. The pore size of the filter used is selected in such a manner that the at least one bacterial species to be detected and the bacteria-bacteriophages-complexes, which consist of bacteria of the at least one bacterial species to be detected and test bacteriophages of the at least one species of test bacteriophages bound thereto, are retained and immobilized on the filter surface, while unbound bacteriophages can pass the filter. Thereby, a separation of bacteria-bacteriophages-complexes of the bacterial species to be detected and other possibly present bacteria from unbound bacteriophages is achieved. The pore size of the filter used is thus selected according to the size and morphology of the respective bacterial species to be detected.

The filter preferably consists of a membrane, a film or a matrix, such as a ball bed or a nano- or micro-structured surface of a filamentary or tubular material (e.g. fiber/hollow fiber).

Preferably, the filter material consists of synthetic or natural polymers such as polyvinyl chloride (PVC), polyvinylidene fluoride (PVDF), polypropylene (PP), polyethersulfone (PES), polyethylene glycol (PEG), polyacrylamide (PAA), polytetrafluoroethylene (PTFE), nylon, polydimethylsiloxane (PDMS), starch, carbohydrate compounds, latex or silicone; metal or metal alloys which can be magnetic, paramagnetic, super-paramagnetic or non-magnetic; glass, such as borosilicate glass; cellulose, such as methyl cellulose or regenerated cellulose or other carbon compounds, such as activated carbon.

Filtration is preferably carried out gravimetrically, by applying a vacuum or by overpressure.

The detection of bacteria-bacteriophages-complexes on the filter surface in the retentate in step D) as well as the detection of unbound test bacteriophages in the filtrate in step E) is based on the detection of the label with which the bacteriophages are provided, respectively. For example, the label may consist of a reporter molecule with fluorescent properties. After suitable excitation of the reporter molecule, the emitted fluorescence signal can then be detected via a sensor. The fluorescence signals can either be detected instantaneously integrated via an optical emission filter or can be measured spectrophotometrically as a wavelength spectrum. Furthermore, both detection strategies can also be combined. The advantage of the first detection strategy is a higher signal-to-noise ratio and faster measurement. The disadvantage of the first detection strategy is a possible restriction to disjunct fluorescence labels, if several different test bacteriophages are used. The advantage of the spectrophotometric detection strategy is that even partially overlapping labels may be used for several different test bacteriophages, since these can be spectrally segregated and, thus, unambiguously assigned in the downstream processing method.

The signals received from steps D) and E), like e.g. the respective detected fluorescence signals and/or fluorescence spectra, are processed by a processor in step F) and the results of the detection are finally output to a user.

The output is preferably executed via an optical display connected to the processor. Alternatively, the detection results can be wirelessly transmitted from the processor to a tablet computer or a remote computer terminal.

If at least one bacterial species to be detected is present in the sample, the labeled test bacteriophages of the at least one species specifically bind to the at least one bacterial species to be detected and thus form corresponding bacteria-bacteriophages-complexes. The filtration separates these complexes together with other bacteria from unbound bacteriophages. Thus, the complexes immobilized on the filter surface can be detected due to the label of the bound test bacteriophages. The excess unbound test bacteriophages can pass through the filter and can be detected in the filtrate due to their labelling. If the sample does not contain any bacterial species to be detected, no complexes are formed and only unbound test bacteriophages are detected in the filtrate. Excess unbound test bacteriophages may also be detected in the retentate during the procedure, especially if the filter is (partially) clogged. Therefore, the measurement signal of unbound test bacteriophages in the retentate may also be included in the detection in addition to that of the filtrate.

The additional detection of unbound test bacteriophages in step E) reduces the risk of obtaining a false-positive signal when the filter becomes clogged. If the sample contains no bacterial species to be detected and the filter is clogged, for example by an undetectable bacterial species or other particles in the reaction mixture, the unbound test bacteriophages cannot pass the filter and remain in the retentate. This results in detection in the retentate, although no specific bacteria-bacteriophage-complexes can be formed. The result is a false-positive detection of the bacterial species to be detected. If the detection of unbound test bacteriophage in the filtrate in step E) is not possible, this indicates that the filter is blocked. Consequently, the additional detection of unbound test bacteriophages in step E) increases the reliability of the detection method according to the invention.

A lack of detection of unbound test bacteriophages in the filtrate in step E) may alternatively be due to the fact that all test bacteriophages have bound to the at least one bacterial species to be detected. Although this possibility is unlikely because of the high phage titre, the suspension preferably further comprises a labelled reference bacteriophage which does not bind to any bacterial species to be detected and which has a label which is disjunct from the test bacteriophages in order to further increase the reliability of the detection method according to the invention. Due to the labelling, the reference bacteriophage is also detectable. The label of the reference bacteriophage is disjunct from the labels of the test bacteriophages, so that the reference bacteriophage can be detected unambiguously and independently of the respective test bacteriophages. Since the reference bacteriophage does not bind to any bacterial species to be detected, i.e. it does not form any complexes with bacteria, it can ideally be detected solely in the filtrate after filtration. However, if no reference bacteriophage is detected in the filtrate, this indicates that the filter is completely clogged.

Even if the filter becomes partially or completely blocked during the procedure, the use of a reference bacteriophage provides a very reliable detection result. For this purpose, the quotient of the total signal intensity of the reference bacteriophage in the retentate and the total signal intensity of the reference bacteriophage in the filtrate is determined and compared with the quotient of the total signal intensity of the at least one test bacteriophage in the retentate and the total signal intensity of the at least one test bacteriophage in the filtrate. If the quotient determined for the at least one test bacteriophage is significantly higher than the quotient determined for the reference bacteriophage, this provides clear evidence of the presence of at least one bacterial species to be detected in the sample used. However, if signals of the at least one test bacteriophage are found both in the retentate and in the filtrate but as a comparable quotient as for the reference bacteriophage, an unspecific clogging of the filter during the procedure, e.g. by undetectable bacteria, can be assumed.

As an alternative to a labelled reference bacteriophage, labelled micro- or nanoparticles can be used. These do not bind to any bacterial species to be detected and can pass through the filter due to their small size.

Another advantage of the inventive method is that it is not limited to certain bacterial species to be detected, but is universally applicable. The only requirement is the existence of a bacteriophage that is complementary to the bacterial species to be detected. Following a biological principle according to which complementary phages are also suspected to be present in the numerous habitats of bacterial species, it must be assumed that there is at least one bacteriophage for each bacterial species, which specifically infects this bacterial species.

However, the bacteria species to be detected are preferably selected from the group comprising *Staphylococcus aureus*, Methicillin-resistant *Staphylococcus aureus* (MRSA), *Staphylococcus epidermidis, Streptococcus pneumoniae, Streptococcus pyogenes, Haemophilus influenzae, Haemophilus parainfluenzae, Klebsiella pneumoniae, Escherichia coli, Escherichia hermannii*, EHEC, *Enterobacter cloacae, Enterococcus faecalis, Enterococcus faecum, Pseudomonas aeruginosa, Proteus mirabilis, Proteus vulgaris, Staphylococcus saprophyticus, Bacteroides fragilis, Enterccocus faecium, Enterobacter aerogenes, Serratia marcescens*, B-*Streptococcus (agalactiae), Chlamydia trachomatis, Chlamydia psittaci, Ureaplasma urealyticum, Mycoplasma hominis, Mycoplasma pneumoniae, Neisseria gonorrhoeae, Neisseria meningitidis, Citrobacter freundii, Moraxella catarrhalis, Stenotrophomonas maltophilia, Pasteurella multocida, Acinetobacter baumannii, Providencia rettgeri, Bordetella pertussis, Bacillus anthracis, Bacillus cereus, Brucella abortus, Brucella melitensis, Clostridium butolinum, Clostridium difficile, Clostridium tetani, Clostridium perfringens, Clamydia trachomatis, Corynebacterium diphtheriae, Francisella tularensis, Gardenella vaginalis, Listeria monocytogenes, Morganella morganii, Mycobacterium leprae, Mycobacterium tuberculosis, Nocardia asteriodes, Salmonella bongori, Salmonella enterica, Shigella* spp., *Vibrio cholerae, Borrelia burgdorferi, Yersinia pestis, Yersinia enterocolitica, Coxiella bumettii, Aeromonas* spp., *Plesiomonas* spp., *Xanthomonas maltophilia, Treponema pallidum, Eikenella corrodens, Spirillum minus, Rickettsia prowazeki, Rickettsia rickettsii, Rickettsia conorii, Cronobacter* spp., *Campylobacter* spp. and *Legionella pneumophilia*.

Particularly preferably, the bacteria species to be detected may be selected from the group consisting of *Staphylococcus aureus*, methicillin-resistant *Staphylococcus aureus* (MRSA), in particular haMRSA=hospital-aqcuired MRSA, caMRSA=community-acquired MRSA, laMRSA=livestock associated MRSA, VRSA=vancomycin-resistant *Staphylococcus aureus, Staphylococcus epidermidis, Staphylococcus saprophyticus* subsp. *saprophyticus, Streptococcus pneumoniae, Streptococcus pyogenes, Streptococcus agalactiae, Streptococcus dysgalactiae, Enterococcus faecalis, Enterococcus faecium, Listeria monocytogenes, Clostridium difficile, Clostridium perfringens, Escherichia coli, Enterobacter cloacae, Enterobacter aerogenes, Haemophilus influenzae, Haemophilus parainfluenzae, Moraxella catarrhalis, Klebsiella pneumoniae, Klebsiella oxytoca, Serratia marcescens, Acinetobacter baumannii, Citrobacter freundii, Pseudomonas aeruginosa, Stenotrophomonas maltophilia, Proteus mirabilis, Proteus vulgaris, Morganella morganii, Providencia rettgeri, Providencia stuartii, Bacteroides fragilis, Chlamydia trachomatis, Ureaplasma urealyticum, Mycoplasma hominis, Neisseria gonorrhoeae, Treponema pallidum* ssp. *pallidum, Salmonella Typhi, Salmonella typhimurium, Pasteurella multocida, Shigella sonnei, Shigella flexneri, Campylobacter jejuni, Vibrio cholera, Francisella tularensis, Bordetella pertussis*, and *Legionella pneumophilas*.

In one embodiment of the inventive method, the one or more suspensions preferably each comprise two or more species of labeled test bacteriophages. The species specifically bind to different bacterial species to be detected. Preferably, the labels of the species are disjunct or partially overlapping and thus characteristic for the respective species of test bacteriophages. This enables the detection of the presence of two or more bacterial species in a sample simultaneously in one batch. Preferably, the one or more suspensions contain up to 6 different species of labelled test bacteriophages each, further preferably up to 5 different species, even more preferably up to 4 different species and most preferably up to 3 different species.

In a further embodiment, the inventive process is carried out in parallel with two or more suspensions, each of which comprises a different species of labelled test bacteriophages, wherein the labels of the species are preferably disjunct or partially overlapping. The sample to be tested is distributed over the two or more suspensions. Preferably, the sample to be tested is distributed via a microfluidic system, so that the sample does not have to be added individually to the suspensions but is added simultaneously through microfluidic channels of the microfluidic system. Preferably, 6 parallel suspensions, further preferably 5 parallel suspensions, even further preferably 4 parallel suspensions and most preferably up to 3 parallel suspensions are used in this embodiment. This also enables the simultaneous detection of the presence of two or more bacterial species within one sample.

In another embodiment, the method further comprises a step following step A) in which the labelled bacteriophages are detected in the suspension prior to the addition of the sample. This step serves to acquire the entirety of signals originating from the labels of the unbound bacteriophages as an initial reference. If the label is e.g. a reporter molecule with fluorescent properties, the total fluorescence of the unbound bacteriophages is detected after appropriate excitation as an initial reference before the sample is added or its fluorescence spectrum is recorded using a spectral photometer.

Preferably, the method also includes the detection of the reaction mixture obtained in step B) or in the optional step G) prior to filtration.

The labelling of the bacteriophages preferably comprises at least one reporter molecule having fluorescent or chemiluminescent properties or at least one reporter molecule which emits light by interaction with a secondary molecule. Further preferred is at least one reporter molecule having fluorescent or chemiluminescent properties. At least one reporter molecule having fluorescent properties is particularly preferred.

The reporter molecules having fluorescent properties include
- organic fluorophores, such as xanthenes, rhodamines, coumarins, acridine derivatives, fluoresceine and Aexa Fluor derivatives, SYBR Green and SYBR Gold;
- inorganic fluorophores and their composites, such as quantum dots (QD);
- fluorescent magnetic particles; and
- fluorescent proteins, such as the green fluorescent protein (GFP), the yellow fluorescent protein (YFP) or derivatives thereof.

Reporter molecules that emit light by interaction with a secondary molecule include
- enzymes, such as alkaline phosphatase or horseradish peroxidase, which emit light by conversion of corresponding marker substrates; and
- biotin, which emits light by binding streptavidin as an interaction partner, which in turn carries a fluorescent or chemiluminescent label.

Organic fluorophores are most preferred for the labelling of bacteriophages.

The bacteriophages can be labelled by coupling at least one reporter molecule to the DNA of the phage, to proteins in the capsid region (head envelope proteins) or to proteins in the tail region of the phage (tail fiber proteins). The coupling of at least one reporter molecule to proteins in the capsid region of the bacteriophages is preferred.

Preferably, the coupling is obtained by forming a covalent bond between the at least one reporter molecule and the bacteriophage. For this purpose
- active esters of the at least one reporter molecule, such as N-hydroxysuccinimide esters (NHS esters) or sulfotetrafluorophenyl esters (STFP esters), for coupling to amino groups;
- isothiocyanates of the at least one reporter molecule for coupling to amino groups;
- maleimides of the at least one reporter molecule for coupling to thiol groups;
- azides of the at least one reporter molecule for coupling to alkynes via a two-stage azide-alkine cycloaddition reaction; and
- photoreactive groups in the at least one reporter molecule for non-specific coupling are used.

Examples are 5(6)-carboxyfluorescein-NHS-esters as an active ester, fluorescein isothiocyanate (FITC) as an isothiocyanate, Alexa Fluor 488-maleimide as a maleimide, 5-azido-tetramethylrhodamine (5-TAMRA-azide) as an azide and photobiotin as a photoreactive group.

In a preferred embodiment of the inventive method, the labelling of the bacteriophages consists of at least one fluorescent reporter molecule. The excitation is carried out by an illumination unit, respectively, which preferably comprises one or more lasers or one or more light-emitting diodes (LEDs). Furthermore, the excitation is conducted in the wavelength range of 200-1000 nm, further preferably in the wavelength range of 350-700 nm. The detection of bacteria-bacteriophages-complexes on the filter surface in the retentate and the detection of unbound bacteriophages in the filtrate are carried out by measuring the fluorescence integrated via an optical emission filter using an optical sensor and/or by measuring the fluorescence intensity spectrum. Fluorescence is preferably measured using fluorescence microscopy and/or an optical sensor and/or a spectral photometer. The optical sensor is further preferably selected from the group consisting of a photomultiplier (PMT), a CCD sensor (charge coupled device) and a CMOS sensor (complementary metal-oxide-semiconductor). The spectral photometer allows the scanning of the fluorescence intensity in predetermined wavelength intervals, preferably in 20 nm steps, further preferably in 10 nm steps, especially preferably in 2-5 nm steps.

In another preferred embodiment, detection is carried out by time-resolved measurement of the light emission, i.e. the light emitted by reporter molecules is continuously detected over a certain period of time. When the labelling of the bacteriophages is at least one fluorescent reporter molecule, the excitation and detection are carried out as described in the previous embodiment, with the proviso that the fluorescence is measured in a time-resolved manner.

Preferably, the inventive method for the detection of bacteria further comprises the step of a pre-separation of bacteria-bacteriophages-complexes and unbound bacteriophages, wherein the pre-separation follows step B) or the optional step G). The pre-separation of the reaction mixture is preferably carried out according to the principle of gel filtration (gel permeation chromatography or size exclusion chromatography) using a gel matrix. This means that bacteria-bacteriophages-complexes and unbound bacteriophages are separated from each other due to their difference in size, whereby the larger complexes leave the gel matrix before the smaller unbound bacteriophages. The gel matrix preferably consists of synthetic or natural polymers such as polyvinyl chloride (PVC), polyvinylidene fluoride (PVDF), polypropylene (PP), polyethersulfone (PES), polyethylene glycol (PEG), polyacrylamide (PAA), polytetrafluoroethylene (PTFE), nylon, polydimethylsiloxane (PDMS), starch, carbohydrate compounds, latex or silicone; metal or metal alloys which can be magnetic, paramagnetic, super-paramagnetic or non-magnetic; glass, such as borosilicate glass; cellulose, such as methyl cellulose or regenerated cellulose or other carbon compounds.

The gel matrix preferably has a pore size of 0.01-5 µm. The choice of the material and of the pore size of the gel matrix depends on the size and morphology of the at least one bacterial species to be detected, so that an optimal pre-separation of the bacteria-bacteriophages-complexes from unbound bacteriophages is achieved.

In a further embodiment, the inventive method furthermore comprises the step of concentrating the bacteria-bacteriophages-complexes and the unbound bacteriophages before the filtration in step C).

The concentration may be conducted mechanically or electromagnetically.

Further preferably, the test bacteriophages of the at least one species and the optional reference phage are coated with magnetic beads. In this case, the concentration may be achieved electromagnetically by applying an external magnetic field, for example by providing an electromagnet.

The optional steps of pre-separation and concentration may be carried out individually or in combination in the inventive method.

In a further embodiment, the inventive process may comprise a rinsing step after the filtration of the reaction mixture in step C). In this rinsing step, the filter is preferably rinsed with a neutral solution. The neutral solution preferably consists of water, a buffer solution or any other aqueous solution or of a previously sterile-filtered sample.

In another aspect, the present invention describes a reaction vessel for carrying out the inventive method for the detection of bacteria.

Preferably, the inventive reaction vessel exhibits a length of 5-20 mm, a width of 5-20 mm and a height of 50-100 mm.

The inventive reaction vessel comprises at least two compartments which are separated from each other by a filter. The filter preferably has a pore size of from 0.1 µm to 0.5 µm, and more preferably of from 0.2-0.5 µm. A pore size of 0.3-0.5 µm is particularly preferred and the most preferred pore size is 0.2-0.4 µm. As previously described for the method, the pore size of the filter used is selected according to the size and morphology of the respective bacterial species to be detected in order to achieve an efficient separation of bacteria-bacteriophages-complexes and other bacteria possibly present from unbound bacteriophages.

The filter preferably consists of a membrane, a film or a matrix, such as a ball bed or a nano- or microstructured surface of a filamentary or tubular material (e.g. fiber/hollow fiber).

Preferably, the filter material consists of synthetic or natural polymers such as polyvinyl chloride (PVC), polyvinylidene fluoride (PVDF), polypropylene (PP), polyethersulfone (PES), polyethylene glycol (PEG), polyacrylamide (PAA), polytetrafluoroethylene (PTFE), nylon, polydimethylsiloxane (PDMS), starch, carbohydrate compounds, latex or silicone; metal or metal alloys which can be magnetic, paramagnetic, super-paramagnetic or non-magnetic; glass, such as borosilicate glass; cellulose, such as methyl cellulose or regenerated cellulose or other carbon compounds, such as activated carbon.

One compartment of the reaction vessel is a phage reservoir containing a suspension which comprises at least one species of labeled test bacteriophages that specifically bind to a bacterial species to be detected. Preferably, the label is characteristic for the respective species of test bacteriophages.

In a further embodiment, the suspension in the phage reservoir comprises two or more species of labeled test bacteriophages which each specifically bind to different bacterial species to be detected, wherein the labels of the species are disjunct or partially overlapping, so that the label is characteristic of the respective species of test bacteriophages.

The concentration of the bacteriophages in the suspension, the volume of the suspension and the other specifications of the suspension correspond to the general information as described for the inventive method.

Likewise, the general information of the method regarding the labelled test bacteriophages and their labelling apply mutatis mutandis to the inventive reaction vessel.

Preferably, the suspension in the phage reservoir further comprises a labelled reference bacteriophage which does not bind to any bacterial species to be detected and which has a label disjunct from the test bacteriophages. The beneficial effects of this embodiment are described in detail for the inventive method.

In one embodiment of the reaction vessel according to the invention, the phage reservoir is sealed by compressible membranes so that the suspension is not in direct contact with the filter. Only by pressing in the compressible membranes upon addition of a sample is to be tested for the presence of at least one bacterial species to be detected, the resulting reaction mixture flows onto the filter.

One compartment of the inventive reaction vessel is a collection reservoir, which is intended to collect the filtrate of the reaction mixture after the addition of a sample to the suspension and subsequent filtration.

Furthermore, the reaction vessel contains a means for its identification.

This is preferably an RFID chip (radio frequency identification) or a barcode. Further preferably, the RFID chip (radio-frequency identification) or the barcode preferably contain data regarding the serial number, the production date, the expiry date, the phage titre in the suspension and/or the bacterial species or strains to be detected. The means for identification enables a simple and unambiguous identification of the reaction vessel, which minimizes the risk of mix-up of reaction vessels and thus increases the reliability of a method of detection carried out with said reaction vessel.

Moreover, the inventive reaction vessel comprises at least two measuring windows, wherein one measuring window is arranged in the region of the filter surface which faces the phage reservoir, and wherein one measuring window is arranged in the region of the collection reservoir. This enables the detection of bacteria-bacteriophages-complexes on the filter surface in the retentate and the detection of unbound bacteriophages in the filtrate when carrying out the detection method according to the invention using the inventive reaction vessel. The inventive reaction vessel my additionally comprise excitation windows in the area of the measurement windows, which enable excitation of reporter molecules with fluorescent properties. Alternatively, excitation may be conducted through the measurement windows.

In a preferred embodiment, the reaction vessel comprises a further compartment between the phage reservoir and the filter, which contains at least one pre-filter. The at least one pre-filter enables the pre-separation of bacteria-bacteriophages-complexes from unbound bacteriophages in the reaction mixture prior to the filtration.

The pre-filter is further preferably a gel matrix, which pre-separates the reaction mixture according to the principle of gel filtration. The gel matrix preferably consists of synthetic or natural polymers such as polyvinyl chloride (PVC), polyvinylidene fluoride (PVDF), polypropylene (PP), polyethersulfone (PES), polyethylene glycol (PEG), polyacrylamide (PAA), polytetrafluoro-ethylene (PTFE), nylon, polydimethylsiloxane (PDMS), starch, carbohydrate compounds, latex or silicone; metal or metal alloys which can be magnetic, paramagnetic, super-paramagnetic or non-magnetic; glass, such as borosilicate glass; cellulose, such as methyl cellulose or regenerated cellulose or other carbon compounds. Furthermore, the gel matrix preferably has a pore size of 0.01-5 µm. The selection of the material and of the pore size of the gel matrix depends on the size and morphology of the at least one bacterial species to be detected, so that an optimal pre-separation of the bacteria-bacteriophages-complexes from unbound bacteriophages is achieved.

In this embodiment, the reaction vessel further comprises one or more measuring windows which are arranged directly below the compartment containing at least one pre-filter.

Preferably, the reaction vessel narrows in direction from the phage reservoir to the filter so that a concentration of the bacteria-bacteriophages-complexes and of the unbound bacteriophages prior to filtration is enabled.

In addition, the reaction vessel is preferably sealed by a septum in the region of the phage reservoir.

The reaction vessel preferably comprises a further measuring window which is arranged in the area of the phage reservoir. This allows the detection of the entirety of signals originating from the labels of the unbound bacteriophages as an initial reference. When the label is, e.g., a reporter molecule with fluorescent properties, the total fluorescence of the unbound bacteriophages is detected as an initial reference after an appropriate excitation and before the sample is added or its fluorescence spectrum is recorded using a spectral photometer.

Furthermore, the reaction vessel preferably comprises one or more compartments which are connected to the collection reservoir and are referred to as subsequent concentration reservoir(s). The last of these compartments is called the waste reservoir. Further preferably, the one or more subsequent concentration reservoir(s) are separated from the collection reservoir or from each other by subsequent filters with a pore size of 0.1 µm to 0.5 µm, preferably 0.2-0.5 µm, further preferably 0.3-0.5 µm and most preferably 0.2-0.4 µm. The subsequent concentration reservoirs can also be equipped with their own measuring windows and excitation windows. Further, the pore size of the subsequent filters can decrease in direction from the collection reservoir to the waste reservoir, which enables a serial separation of different bacteria and bacteria-bacteriophages-complexes according to the size and morphology of the respective bacterial species to be detected. The waste reservoir is separated by a final filter with a pore size of ≤0.05 µm from the collection reservoir or, if present, from the one or more subsequent concentration reservoir(s). All bacteriophages are removed by the final filter, so that the remaining filtrate can be disposed of safely and at low cost. Alternatively, the waste reservoir contains an absorbent which absorbs the filtrate from the collection reservoir or, if present, from the one or more subsequent concentration reservoir(s).

In a further embodiment, the reaction vessel comprises another compartment between the filter and the phage reservoir, which is preferably separated from other compartments by a septum. Further preferably, this compartment contains an indicator solution with labeled micro- or nanoparticles which do not bind to any bacterial species to be detected and which may pass through the filter due to their small size. Therefore, the indicator solution with the labelled micro- or nanoparticles can be used as an alternative to a reference bacteriophage and is added by puncturing the membrane.

The different embodiments of the inventive reaction vessel are not mutually exclusive and can hence be implemented individually or in combination.

In a further aspect, the present invention refers to a cartridge comprising two or more inventive reaction vessels arranged parallel and/or in series to each other, wherein each parallel reaction vessel contains different species of labelled test bacteriophages in the suspension of the phage reservoir, each of which specifically binds to different bacterial species to be detected. This enables the detection of the presence of two or more bacterial species within one sample simultaneously. The labels of the different species of labelled test bacteriophages are preferably disjunct or partially overlapping. The serial arrangement of reaction vessels enables the separation of different bacteria and bacteria-bacteriophages-complexes according to the size and morphology of the respective bacterial species to be detected. In this case, the pore size of the filter of the downstream reaction vessel or reaction vessels is smaller than the pore size of the filter in the preceding reaction vessel.

The cartridge preferably comprises up to 6 parallel arranged reaction vessels, further preferably up to 5 parallel arranged reaction vessels, even further preferably up to 4 parallel arranged reaction vessels and most preferably up to 3 parallel arranged reaction vessels.

Moreover, the cartridge preferably comprises a microfluidic system into which the sample to be tested is injected and which guides the sample via microfluidic channels to the phage reservoirs of the parallel arranged reaction vessels, so that there is no need for adding the sample to the suspensions individually.

The present invention also concerns a measuring device for carrying out the inventive method for the detection of bacteria.

The measuring device comprises a slot into which an inventive reaction vessel or an inventive cartridge is inserted.

Further, the measuring device comprises at least two detection optics each of which is arranged in the region of the measuring windows of the inserted reaction vessel or cartridge, and a processor.

When the measuring device comprises a slot for a reaction vessel, it may contain three, four or more detection optics depending on the embodiment of the reaction vessel, i.e. according to the number of measuring windows.

On the other hand, when the measuring device comprises a slot for a cartridge, the number of detection optics depends on the number of reaction vessels arranged in parallel and/or in series within the cartridge, whereby the measuring device may contain two to four or more detection optics per reaction vessel arranged in parallel.

The detection optics each comprise a lens system for focusing light emitted by the label of the bacteriophages onto at least one sensor, the at least one sensor detecting the emitted light. The at least one sensor of the detection optics preferably comprises one or more optical sensors and/or one or more spectral photometers, which are equipped with or without emission filters, thereby enabling a resolution of the spectrum of fluorescence signals. In the case of a combination of an optical sensor and one or more spectral photometers, the detection optics can be sequentially controlled such that it may be switched between fast detection with high signal-to-noise ratio (lens-focused detection of total fluorescence intensity in the optical sensor) or slow detection with itemization of the spectrum (spectral photometer). Herein, a spectral photometer is not construed as an optical sensor in a strict sense.

Preferably the optical sensors are selected from the group consisting of a photomultiplier (PMT), a CCD sensor (charge coupled device) and a CMOS sensor (complementary metal-oxide-semiconductor).

Furthermore, the detection optics preferably each comprise an illumination unit that emits light in the wavelength range of 200-1000 nm and a further lens system for focusing the light emitted by the illumination unit onto a measuring area. Thereby, the illumination unit is also connected to and controlled by the processor.

The illumination unit preferably emits light in the wavelength range of 350-700 nm. Further preferably, the illumination unit comprises a laser or one or more light-emitting diodes (LEDs).

The processor is connected to the at least one sensor of the detection optics and processes the received detection signals.

Moreover, the measuring device comprises an output unit connected to the processor that outputs the detection results to a user.

The output unit preferably comprises an optical display.

Further preferably, the output unit includes a radio interface, whereby the detection results can be transmitted wirelessly by radio from the processor to a tablet computer or a remote computer terminal.

Preferably, the measuring device further comprises an integrated reader that detects the means for identifying the reaction vessel and forwards the detected data to the processor, wherein the processor processes the detected data and the results of the identification are output to a user via the output unit.

In a preferred embodiment, the measuring device further comprises an electromagnet that may be selectively switched on and off, such as a ring coil. The electromagnet is further preferably arranged in the region of the filter surface of the reaction vessel inserted into the slot which faces the phage reservoir.

In the following, the present invention is described in detail with reference to the figures and various embodiments are further explained.

FIG. 1 shows an embodiment of the inventive method. A sample (3), which is to be tested for the presence of a bacterial species to be detected, is injected into a suspension (1) which is provided in a purgeable phage reservoir (8). The sample (3) may contain other, undetectable bacterial species. In this embodiment, the suspension (1) contains one species of labeled test bacteriophages (2) which bind specifically to the bacterial species to be detected. The labelling is a reporter molecule with fluorescent properties. After mixing the sample (3) with the suspension (1) and incubating the reaction mixture, it flows onto the filter (4) having a preferred pore size between 0.1 μm and 0.5 μm and is filtered gravimetrically and/or under the action of an external punch pressure or vacuum ('dead end filtration'). Thereby, the obtained bacteria-bacteriophages-complexes (5) and other, undetectable bacteria species are immobilized on the filter surface in the retentate, whereas the remaining unbound test bacteriophages (2) pass through the pores of the filter (4) and are collected as a filtrate in a collection reservoir (9). The detection of the bacteria-bacteriophages-complexes (5) on the filter surface and of the unbound test bacteriophages (2) in the filtrate is carried out by specific excitation of the fluorescent reporter molecules used and by measuring the resulting fluorescence. Usually, the excitation is conducted in the wavelength range where the absorption maximum of the respective fluorescent reporter molecule is found. In this embodiment, the suspension (1) further contains a labelled reference bacteriophage (6), which does not bind to the bacterial species to be detected, therefore passes through the pores of the filter (4) and which is also collected as a filtrate in the collection reservoir (9). The labelling of the reference bacteriophages (6) also consists of a reporter molecule with fluorescent properties, wherein the reporter molecules of the test bacteriophages (2) and of the reference bacteriophages (6) are preferably disjunct. This means that the respective fluorescent reporter molecules are selected in such a manner that they may absorb light at the same or different excitation wavelengths but emit light at different wavelengths. Owing to this, the emitted fluorescence signals of the respective reporter molecules and, hence, of the respective bacteriophages can be clearly differentiated. Accordingly, the reference bacteriophage (6) is also detected by specific excitation of its fluorescent reporter molecules and by measuring the resulting fluorescence. The obtained fluorescence signals from the retentate and from the filtrate are then processed by a processor and the results of the detection are output to a user.

In spectrophotometric detection of the fluorescence, i.e. when a spectral photometer is used as a sensor, a further detection over an adjustable spectral band wavelength range may be carried out in order to gather the emission spectrum. In this case, overlapping fluorescence reporter molecules may be used instead of disjunct fluorescence reporter molecules, as these may be detected in the multiplexing method and may be spectrally segregated subsequently by the processor.

The output may be conducted via an optical display connected to the processor or wirelessly to a tablet computer or a remote computer terminal. Based on the quotients of the total intensity of the measured fluorescence in the retentate and of the total intensity of the measured fluorescence in the filtrate, calculated for the test bacteriophage (2) and for the reference bacteriophage (6), respectively, and by a comparison of these, a reliable result of the detection method can be achieved. If the quotient determined for the test bacteriophage (2) is significantly higher than the quotient determined for the reference bacteriophage (6), this provides clear evidence of the presence of the bacterial species to be detected in the sample. However, if fluorescence signals of the test bacteriophage (2) are found both in the retentate and in the filtrate, but in a ratio comparable to that of the reference bacteriophage (6), it can be assumed that the filter (4) has become clogged during the procedure in an unspecific manner, e.g. by bacteria that are not supposed be detected.

Figure 2:
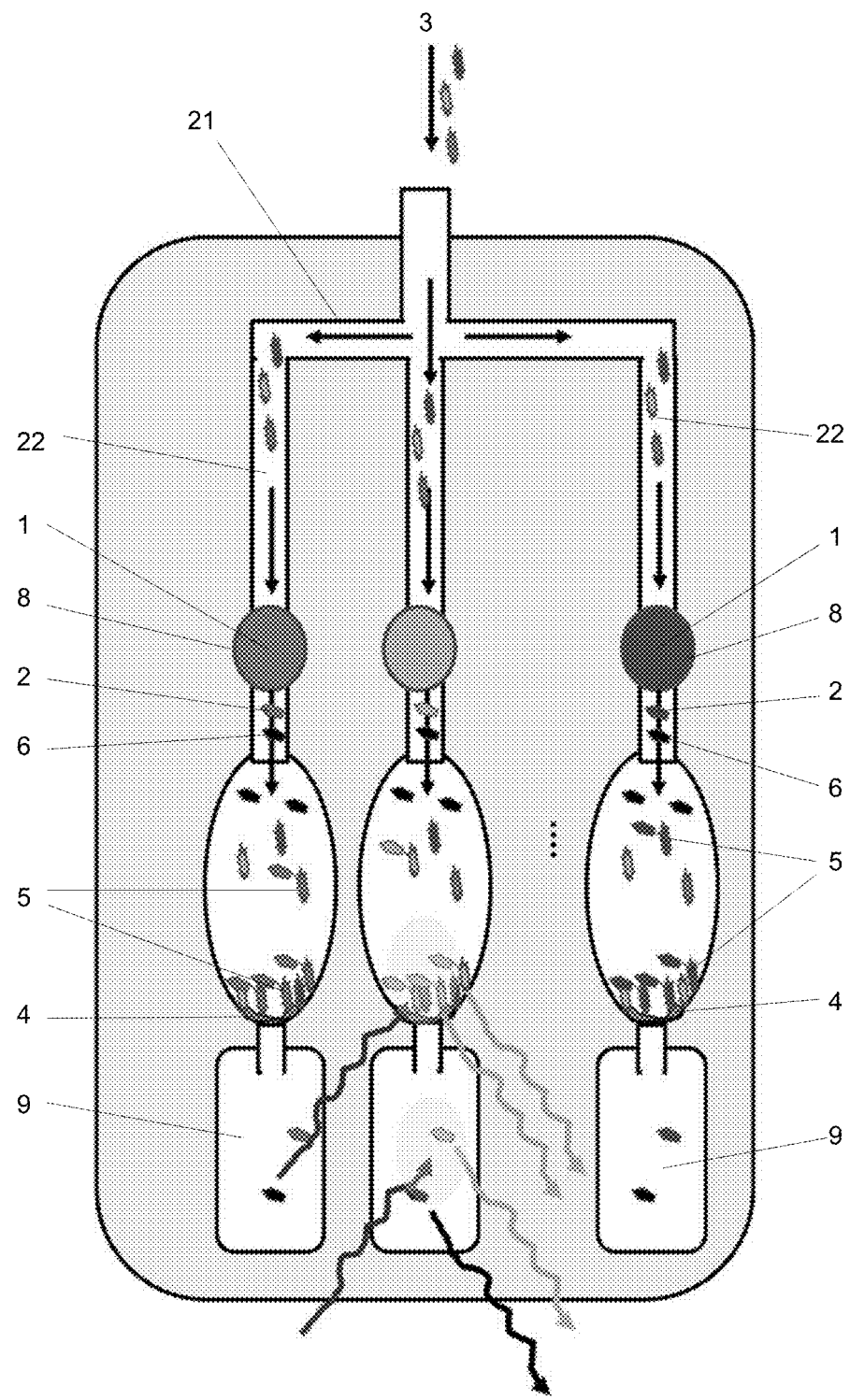

Another embodiment of the inventive method is shown in FIG. 2. Here, the individual steps of the method are carried out in the same manner as in the above-described embodiment of FIG. 1, with the difference that three different suspensions (1) are used in parallel. Said suspensions (1) each contain a different species of labeled test bacteriophages (2), which specifically bind to a different bacterial species to be detected, and a reference bacteriophage (6). The labels are fluorescent reporter molecules, respectively, which are preferably disjunct or may also partially overlap, when spectrophotometric detection with subsequent segregation is enabled. In this preferred embodiment, the sample (3) to be tested is distributed to the three suspensions (1) by microfluidic channels (25) of a microfluidic system (24) so that the addition takes place simultaneously. Due to the preferably disjunct or partially overlapping labels, a specific detection of three bacterial species to be detected within one sample (3) is therefore enabled simultaneously.

Figure 3:
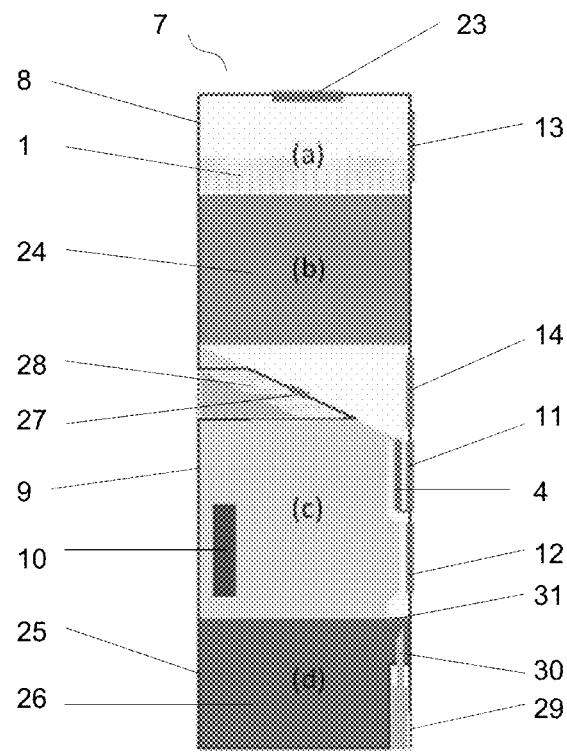
Figure 3:
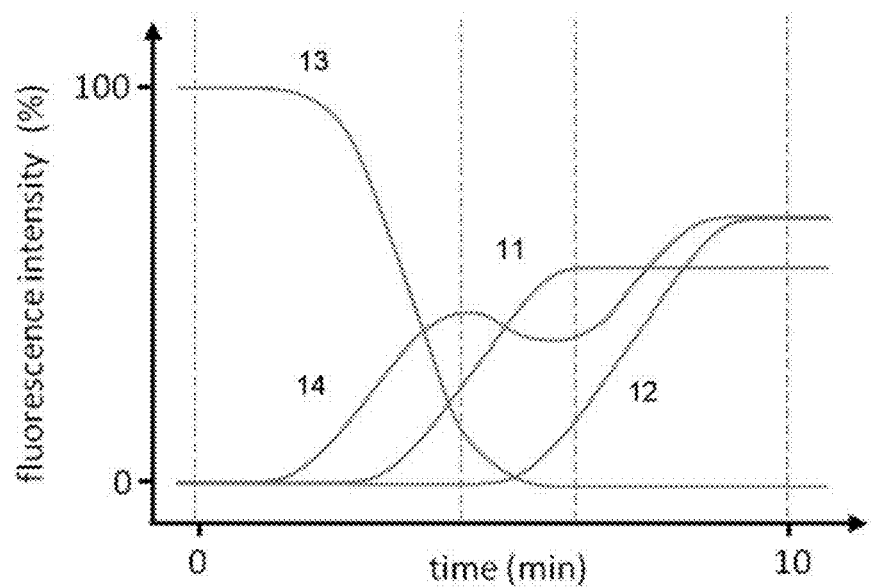

FIG. 3 A shows a preferred embodiment of the reaction vessel (7) according to the invention. It comprises four compartments (a)-(d). Compartment (a) is a phage reservoir (8) containing a suspension (1), which comprises at least one species of labeled test bacteriophages that specifically binds to a bacterial species to be detected, the label preferably being characteristic of the respective species of test bacteriophages. Further, the suspension (1) in the phage reservoir (8) may contain a labelled reference bacteriophage which does not bind to any bacterial species to be detected and which has a label which is disjunct from the test bacteriophages. The phage reservoir (8) is sealed by a septum (23). Compartment (b) contains a gel matrix (24) having a pore size of 0.01-5 μm as a pre-filter, which enables a pre-separation of the reaction mixture according to the principle of gel filtration. Accordingly, bacteria-bacteriophages-complexes and undetectable bacteria are separated from unbound bacteriophages due to their difference in size, whereby the larger complexes leave the gel matrix (24) prior to the smaller, unbound bacteriophages. Compartment (c) is a collection reservoir (9) which is designed to collect the filtrate of the reaction mixture after the addition of a sample to the suspension (1) and subsequent filtration. Compartment (d) is a waste reservoir (25) containing an absorbent (26) which absorbs the filtrate from the collection reservoir (9). The compartments (a) and (b) are separated from the compartments (c) and (d) by a filter (4) having a pore size of from 0.1 µm to 0.5 µm. In the embodiment shown, the reaction vessel further exhibits an RFID chip (10) for identification and an additional compartment separated from the other compartments by a septum (27), which contains an indicator solution (28) with labeled micro- or nanoparticles. These do not bind to any detectable bacterial species to be detected and pass through the filter (4) due to their small size. Therefore, the indicator solution (28) containing the labeled micro- or nanoparticles may be used as an alternative to a reference bacteriophage and it may be added to the reaction solution by puncturing the membrane (27). In this embodiment, the reaction vessel narrows towards the filter (4) so that a concentration of the bacteria-bacteriophages-complexes and of the unbound bacteriophages is enabled prior to filtration. Furthermore, the shown reaction vessel (7) comprises four measuring windows (11-14) in total. One measuring window (11) is arranged in the region of the filter surface facing the phage reservoir. Another measuring window (12) is located in the region of the collection reservoir. This enables the detection of bacteria-bacteriophages-complexes immobilized on the filter surface in the retentate and of unbound bacteriophages in the filtrate. Another measuring window (13) is arranged in the region of the phage reservoir, so that the entirety of signals originating from the labels of the bacteriophages is detected as an initial reference prior to adding a sample to be tested. In addition, a fourth measuring window (14) is located below the gel matrix for the detection of bacteria-bacteriophages complexes and unbound bacteriophages in the reaction mixture when these elute from the gel matrix (24) prior to filtration. In the embodiment shown, the reaction vessel (7) further has an integrated aeration mechanism (29) in the region of the waste reservoir (25) consisting of an aeration needle (30) and a septum (31). When the septum (31) is punctured, the reaction vessel is aerated and gravimetric filtration is started.

FIG. 3 B shows the theoretical course of a time-resolved measurement of the fluorescence in a preferred embodiment of the inventive method using the inventive reaction vessel (7) of FIG. 3 A. Here, a sample, which is tested for the presence of a bacterial species to be detected, is injected through the septum (23) into the suspension (1) in the phage reservoir (8), mixed with the suspension (1) by multiple (3-5×) swivelling and incubated for 5-10 min at room temperature (RT). The at least one species of test bacteriophages in the suspension (1) exhibits fluorescent reporter molecules as labels. By puncturing the septum (31) in the integrated aeration mechanism (29), a time-resolved measurement of the fluorescence intensity at the four measuring windows (11-14) of the reaction vessel (7) is started simultaneously. As a result of the aeration, the reaction mixture flows through the compartments (b) and (c) one after the other, such that the fluorescence at measurement window 13 in compartment (a) decreases continuously over time until it can no longer be detected. In the gel matrix (24) in compartment (b), unbound phages are separated from larger bacteria-bacteriophages-complexes due to their difference in size. The larger bacteria-bacteriophages-complexes elute from the gel matrix (24) prior to the smaller unbound bacteriophages. Thereby, the fluorescence at the measuring window (14) initially increases until all bacteria-bacteriophages-complexes have passed this measuring area. The fluorescence then slightly decreases until the unbound bacteriophages finally leave the gel matrix, which is characterized by a renewed increase in fluorescence at measuring window (14). The bacteria-bacteriophages-complexes are immobilized on the filter (4), so that their fluorescence signal increases at the measuring window (11) until all bacteria-bacteriophages-complexes and bacterial species not to be detected, respectively, are immobilized on the filter (4). Unbound bacteriophages pass through the filter (4) and appear as an increasing fluorescence signal in the measurement window (12) in the collection reservoir (9). Excess reaction mixture, which has passed through the reaction vessel completely, is collected in compartment (d) and bound by an absorbent (26).

Moreover, FIG. 4 A shows the schematic representation of a preferred embodiment of the inventive cartridge (36) for the detection of bacteria in a) front view, b) top view and c) side view. The cartridge (36) according to the invention comprises two reaction vessels (I, II) arranged in parallel, each of which essentially corresponds to the embodiment of the inventive reaction vessel (7) as shown in FIG. 3 A. The parallel reaction vessels (I, II) each contain four measuring windows (11-14). One measuring window (11) is arranged in the region of the filter surface facing the phage reservoir. Another measuring window (12) is located in the region of the collection reservoir. This enables the detection of bacteria-bacteriophages-complexes immobilized on the filter surface in the retentate and of unbound bacteriophages in the filtrate. Another measuring window (13) is located in the region of the phage reservoir, so that the entirety of signals originating from the labels of the bacteriophages may be detected as an initial reference prior to adding a sample to be tested. In addition, a fourth measuring window (14) is located below the gel matrix for the detection of bacteria-bacteriophage-complexes and unbound bacteriophages in the reaction mixture upon elution from the gel matrix (24) and prior to filtration. In the embodiment shown, the parallel reaction vessels (I, II) each further exhibit four excitation windows (11a-14a) in the region of the measuring windows (11-14), which serve to excite reporter molecules with fluorescent properties.

FIG. 4 B shows the theoretical courses of a time-resolved measurement of the fluorescence in a preferred embodiment of the inventive method using the inventive cartridge (7) of FIG. 4 A. This involves injecting a sample, which is tested for the presence of a bacterial species to be detected, into the reaction vessel (I). A neutral solution without bacteria to be detected is injected into the reaction vessel (II) so that no bacteria-bacteriophages-complexes can form. Both reaction vessels (I and II) are rinsed with neutral solution. As already described in detail for the course in FIG. 3 B, the fluorescence at measuring window (13) continuously decreases during the filtration over time in both reaction vessels (I and II) until it can no longer be detected. In the case of the reaction vessel (I), the larger bacteria-bacteriophages-complexes elute from the gel matrix prior to the smaller unbound bacteriophages due to the pre-separation by gel filtration. Thereby, the fluorescence at measuring window (14) initially increases until all bacteria-bacteriophages-complexes have passed this measuring area. The fluorescence then slightly decreases until the unbound bacteriophages finally leave the gel matrix, which is characterized by a renewed increase in fluorescence at measuring window (14). Since no bacteria-bacteriophages-complexes can form in the reaction vessel (II) due to the lack of addition of a sample, the increase in fluorescence at measuring window (14) is solely due to unbound test bacteriophages; a "shoulder" in the intensity of the fluorescence at measuring window (14) is therefore not observed. In the course of rinsing with neutral solution, the unbound bacteriophages (in the case of reaction vessel (I) also any remaining bacteria-bacteriophage-complexes) are gradually removed from this measuring area, resulting in a decrease in the fluorescence towards zero at measuring window (14). The bacteria-bacteriophages-complexes formed in reaction vessel (I) are immobilized on the filter so that the fluorescence signal at measuring window (11) increases until all bacteria-bacteriophages-complexes are immobilized on the filter. After that, no further increase in the fluorescence at measuring window (11) of the reaction vessel can be observed. Rather, the fluorescence in this measuring area remains constant even during rinsing with neutral solution. In contrast, the fluorescence signal at measuring window (11) of the reaction vessel (II) also increases initially, which is, however, due to a temporary accumulation of test bacteriophages in the area of the filter. By rinsing with neutral solution, however, all test bacteriophages pass through the filter, so that the fluorescence in this measuring area decreases while the fluorescence intensity at measuring window (12) at the region of the subsequent collection reservoir of the reaction vessel (II) increases. By rinsing with neutral solution, the test bacteriophages are finally transferred to the waste reservoir. Thereby, the fluorescence signal at measuring window (12) of the reaction vessel (II) decreases again. A similar course of the fluorescence signal at measuring window (12) can also be observed for reaction vessel (I). However, this fluorescence originates from the remaining, unbound bacteriophages only.

A schematic representation of the assembly of inventive reaction vessel (7) and measuring device (15) in another preferred embodiment is shown in FIG. 5. The illustrated reaction vessel (7) contains a phage reservoir (8) with crushable membranes, which in turn contains a suspension (1) comprising at least one species of labelled test bacteriophages (2) that specifically binds to a bacterial species to be detected, the label preferably being characteristic for the respective species of test bacteriophages (2). Furthermore, the suspension (1) may contain a labelled reference bacteriophage (6) in the purgeable phage reservoir (8), which does not bind to any bacterial species to be detected and which has a label that is disjunct from the test bacteriophages (2). The reaction vessel (7) is sealed at the top with a septum (23) followed by a coarse filter (32) having a pore size of 0.5-10.0 µm to remove larger suspended particles and any impurities. A multi-stage coarse filter (32) having decreasing pore sizes of 0.5-10 µm can also be used. By injecting a sample (3) to be tested into the suspension (1) in the phage reservoir (8), the membranes of the phage reservoir (8) are crushed. Due to gravitation, the resulting reaction mixture begins to flow in the direction of the filter (4), which has a pore size of 0.2 µm. In the illustrated embodiment, the reaction vessel (7) narrows in the downward direction so that a concentration of the bacteria-bacteriophages-complexes (5) and of the unbound bacteriophages (2, 6) prior to filtration is enabled. In addition, a concentration is achieved electromagnetically by selectively switching a homogeneous magnetic field on and off. For this purpose, the measuring device (15) comprises a ring coil (33) as an electromagnet, which is arranged in the region of the filter surface of the filter (4). Moreover, the test bacteriophages (2) of at least one species as well as the optional reference phage (6) are coated with magnetic beads. A collection reservoir (9) follows Filter (4) for collecting the filtrate after the filtration. The collection reservoir (9) is followed by another compartment, which is called the waste reservoir (25) and which is separated from the collection reservoir (9) by a final filter (34) having a pore size of ≤0.05 µm. All bacteriophages are removed by the final filter (34) so that the remaining filtrate can be disposed of safely and at low cost. In this embodiment, the labelling of the bacteriophages (2, 6) also consists of at least one reporter molecule with fluorescent properties. Accordingly, the measuring device (15) comprises two detection optics (16) besides a shaft into which the reaction vessel (7) is inserted, each of which is arranged in the region of the measuring windows (11, 12) of the inserted reaction vessel (7). In the present embodiment, this means that one detection optics (16) is arranged in the measuring area at the filter surface of the filter (4) for detecting bacteria-bacteriophages-complexes (5), while the second detection optics (16) is arranged in the measuring region at the filter surface of the end filter (34) for detecting unbound bacteriophages (2, 6). The detection optics (16) each contain an LED (19) as an illumination unit, which emits light in the wavelength range of 200-1000 nm, preferably 350-700 nm, depending on the absorption properties of the fluorescent reporter molecules used. If possible, maximum absorption shall be achieved in order to generate a equally strong fluorescence signal. Further, the detection optics (16) each contain a lens system (20) for focusing the light emitted by the LED onto the measuring areas described above together with a further lens system (17) for focusing the light emitted by the fluorescent reporter molecules onto at least one sensor (18), such as a photomultiplier, a CCD sensor or a CMOS sensor as an optical sensor. Alternatively or additionally, a spectral photometer (18) may be applied as a sensor for recording the emission spectrum. Here, a spectral photometer is not construed as an optical sensor in the strict sense. The sensors (18) of the two detection optics (16) each detect the incident light and forward the received detection signals to a processor, which is connected thereto. The processor finally processes the received detection signals and forwards the detection results to a display connected to the processor, which outputs them optically to a user (not shown). Furthermore, one or both detection optics (16) may contain a beam splitter (35) for the spectral separation of several colour channels.

In FIG. 6, an RFID chip is illustrated as an embodiment for the means for identifying the reaction vessel according to the invention. The RFID chip contains data regarding the serial number, the production date, the expiry date, the phage titre in the suspension, and/or the bacterial species(s) or strains to be detected. The RFID chip enables simple and unambiguous identification of the reaction vessel, which minimizes the risk of mix-ups of reaction vessels and thus increases the reliability of a detection procedure carried out with such a reaction vessel.

Experimental Part

1. Isolation of Bacteriophages

Since bacteriophages do not have their own metabolism, they can only be cultured and proliferated on a suitable host bacterium. The host bacteria need a culture medium in which they can grow optimally. The better the growth of the bacteria, the higher the yield of bacteriophages. In a first step, powdery culture medium is dissolved in water and sterilized in an autoclave. The sterile culture medium is then pumped directly from the autoclave into a fermenter and is preheated to the optimum temperature for the growth of the host bacteria (e.g. 30° C.). As soon as the culture medium has reached operating temperature, host bacteria are added to the fermenter from a bacterial pre-culture. These bacteria are now beginning to divide. After a short adaptation period, the host bacteria grow exponentially, i.e. with the highest possible growth rate specific to the bacterial type.

The growth of the bacterial cells is monitored by measuring the optical density at a wavelength of 600 nm ($OD_{600}$) in a photometer. When a cell density, which has been optimized in pre-experiments, is reached, e.g. $5 \times 10^8$ bacteria per millilitre of culture medium, the bacteriophages are added to the fermenter from a bacteriophage pre-culture. The concentration of bacteriophages in the pre-culture is determined in advance using the classical titration method, being a biological activity detection method (see e.g. Martha R. J. Clokie, Andrew M. Kropinski (eds.), Bacteriophages: Methods and Protocols, Volume 1: Isolation, Characterization, and Interactions, vol. 501, C 2009 Humana Press, a part of Springer Science+Business Media). The concentration is adjusted so that ideally every bacterium in the fermenter is recognized and infected by at least one bacteriophage. After successful infection, the host bacteria now produce new bacteriophages instead of new bacteria as before. The proliferation of the bacteriophages takes about one hour. During this time, about 100 new bacteriophages are produced per bacterial cell.

At the end of the process, the bacteria lyse and release the new bacteriophages into the culture medium. The solution produced in the fermenter is highly viscous, as it contains not only the new bacteriophages but also all components of the lysed bacterial cell (fragments of the cell wall, lipids, ribosomes, bacterial genetic material, etc.) as well as the original components of the culture medium (sugar, salts and proteins). For this reason, the bacteriophages must first be purified using a multi-stage filtration process before they are available for a labelling reaction. After the purification, a sterile filtration is carried out, e.g. using 0.2 µm Sartobran® filter cartridges from Sartorius Stedim Biotech, combined with the filling into storage containers (kegs).

In this form, bacteriophages are stable, can be easily transported and stored for months without loss of activity.

2. Labelling of Bacteriophages with Reporter Molecules

In order to avoid side reactions during the coupling with reporter molecules and poor coupling efficiencies, the phages are purified and the buffer is adjusted before being labelled with the activated reporter molecules. During the isolation of proteins, a buffer exchange must be carried out in many cases, e.g. if several chromatographic methods with different buffers are to be used in succession.

The phages used for the labelling experiments are purified and, if necessary, concentrated using the following standard methods:
  ultra-filtration, where the molecular weight cut-off (MWCO) should be >100 kDa
  polyethylene glycol/sodium chloride precipitation
  size exclusion chromatography (gel filtration)
  ion exchange chromatography
  dialysis The separation of small excess molecules, such as salts, dyes or biotin, from phage solutions is carried out by precipitation with polyethylene glycol and sodium chloride and subsequent centrifugation (Jaye, D. L., Edens, H. A., Mazzucchelli, L., Parkos, C. A., 2001. Novel G protein-coupled responses in leukocytes elicited by a chemotactic bacteriophage displaying a cell type-selective binding peptide. J. Immunol. 166, 7250).

After the incubation of the coupling reaction, the phage conjugates are precipitated at least twice with polyethylene glycol 8000 (PEG 8000) and a NaCl solution. This minimizes the amount of free reporter molecules in the conjugate solution. Finally, the conjugate pellet is re-suspended in a suitable buffer. Gel filtration columns with a size exclusion material based on dextran having a MWCO>25 kDa may also be used. Ion exchange chromatography-based purification also permits rapid separation of the conjugates from small molecules, wherein the most suitable gradient and the type as well as the strength of the ion exchange material depends on the applied marker molecules and on the nature of the specific phages. An optimization of the parameters in advance is necessary.

Example 1

$1 \times 10^{11}$ pfu of previously purified and concentrated TB54 bacteriophages (see above) were re-suspended in 10 ml PBS with 0.1 M $NaHCO_3$ (pH 8.5). Thereupon, 100 nmol 5(6)-carboxyfluorescein NHS ester per $1 \times 10^{10}$ pfu were added. The coupling reaction proceeds at room temperature in the dark for one hour. As shown schematically in FIG. 7, the NHS ester of 5(6)-carboxy-fluorescein (2) reacts with the primary amino groups of proteins on the surface of the TB54 phages (1) forming stable amide bonds.

The conjugates are purified either by precipitation or by chromatographic methods as described above. Subsequently, the conjugate is characterized photo-physically by UV/vis and fluorescence spectroscopy.

In FIG. 8, the excitation spectrum and the emission spectrum of 5(6)-carboxyfluorescein-labelled TB54 bacteriophages are illustrated. The spectra show the excitation maximum and emission maximum of 5(6)-carboxy-fluorescein at a wavelength of 495 nm and in the range of 520-530 nm, respectively. These wavelengths were also used in the following for fluorescence microscopic studies of the bacteria-bacteriophages interaction.

Example 2

A fluorescein-isothiocyanate (FTIC) solution in 0.1 M carbonate buffer, pH 9.0 is prepared. An appropriate aliquot is added to the phage solution prepared in example 1 and carefully mixed. The phage suspension is incubated for one hour at room temperature in the dark. The purification and characterization of the conjugate is carried out as described in example 1.

3. Specificity of the Bacteria-Bacteriophages Interaction

To demonstrate the enormous host specificity of a labelled species of test bacteriophage, overnight cultures of *Escherichia coli* bacteria of the strains C600 (PTC Phage Technology Center GmbH), ECOR34 (PTC Phage Technology Center GmbH) and XL10-Gold (Agilent) were prepared in 10 ml TSB (Tryptic Soy Broth) (Sigma-Aldrich) under standard conditions at 37° C. in a preparatory step. The overnight cultures were diluted the following day (1:10 in TSB) and incubated at 37° C. for a further two hours. The bacterial suspensions obtained in this way were then mixed in equal parts (1:1:1). For the fluorescence microscopic detection of the bacteriophage-host interaction, 10 µl of the mixed bacterial culture of the *E. coli* bacteria (C600, ECOR34, XL10-Gold) were added to 990 µl of a suspension of 5(6)-carboxyfluorescin-labelled TB54 bacteriophages in PBS, pH 7.4 (bacterial titre: $\sim 1 \times 10^6$ cells/ml; phage titre: $\sim 1 \times 10^8$ pfu/ml) and incubated for 5 min at room temperature (RT). From the reaction mixture, 20 µl were then transferred onto a microscope slide and examined by fluorescence microscopy (Eclipse Ti, 100× objective lens, Nikon).

FIG. 9 A shows the fluorescence microscope image obtained after incubation of the *E. coli* bacterial strains C600, ECOR34 and XL10-Gold with 5(6)-carboxyfluorescin-labelled TB54 bacteriophages. The image section in the lower left corner shows an enlarged representation of the image area defined by the white frame.

In FIG. 9 B, a corresponding bright field image after incubation of the E. coli bacterial strains C600, ECOR34 and XL10-Gold with 5(6)-carboxyfluorescin-labelled TB54 bacteriophages is illustrated. The image section in the lower left corner shows an enlarged representation of the image area defined by the white frame. The white arrows indicate unlabelled bacteria which differ morphologically from the E. coli C600 bacterial cells infected with labeled TB54 phages. These unlabelled bacteria can be assigned to the strains ECOR34 or XL10-Gold (size marker: 10 µm).

The test results evidence the enormous specificity of the TB54 bacteriophages labelled with 5(6)-carboxyfluorescin. These bind exclusively to the E. coli C600 bacterial strain, whereas the ECOR34 and XL10-Gold strains are not infected. Therefore, only bacteria of the E. coli C600 strain exhibit fluorescence signals in the reaction mixture due to the formation of complexes. Thus, due to the enormous host specificity of bacteriophages, the inventive method offers a clear and reliable detection of bacterial species. It is even possible to detect individual strains within a bacterial species.

FIG. 10 A also shows optical cross sections of the E. coli C600-TB54 bacteriophage complexes obtained in this experiment. The optical sections were prepared at distances of 0.3 µm (size marker 2 µm). In the upper row, the complexes are shown in transmitted light, while the lower row shows the same complexes in fluorescence microscopic view.

The distribution of the punctiform fluorescence signals indicates a localisation of the fluorescent reporter molecules (5(6)-carboxyfluorescin) on the bacterial surface.

FIG. 10 B shows three-dimensional reconstructions of the received E. coli C600-TB54 bacteriophage complexes at different perspectives, which confirms the surface localization of the fluorescent reporter molecules.

4. Sensitivity of the Procedure

To determine the sensitivity of the method for the detection of bacteria, a dilution series was prepared by serial dilution of an initial suspension of 5(6)-carboxyfluorescin-labelled TB54 bacteriophages (PBS, pH 7.4, phage titre: $\sim 1 \times 10^8$ pfu/ml) using PBS, pH 7.4. Of the respective dilution stages with $\sim 1 \times 10^7$ pfu/ml, $\sim 1 \times 10^8$ pfu/ml, $\sim 1 \times 10^8$ pfu/ml, $\sim 1 \times 10^4$ pfu/ml and $\sim 1 \times 10^3$ pfu/ml, 1 ml each was transferred into a measuring cuvette and examined by fluorescence spectroscopy (Qwave compact USB spectrometer, RGB laser system). As a reference, 1 ml PBS buffer without labeled TB54 bacteriophages was used.

The obtained fluorescence spectra are illustrated in FIG. 11 A. For all dilution stages, a distinct maximum of emission in the wavelength range between 520 and 530 nm is detectable, which corresponds to the emission maximum of 5(6)-carboxyfluorescin. Hence, FIG. 11 B shows the integral of the fluorescence in the wavelength range between 520 and 530 nm for the different phage titres.

Thereby, the obtained fluorescence integral for an amount of phages of only $\sim 1 \times 10^3$ pfu can still be clearly distinguished from the reference, i.e. a specific detection starting from only $\sim 1 \times 10^3$ bacteriophages is made possible.

With an average amount of $\sim 1 \times 10^2$ bound bacteriophages per infected bacterium, this means that the inventive method can provide a specific detection starting from a bacterial concentration of only ~10 bacterial cells/ml. The inventive method is therefore not only highly specific, but also highly sensitive.

5. Specific Detection of a Bacterial Species or a Strain of a Bacterial Species

In the following, the specific detection of the bacterial strain Escherichia coli C600 at different bacterial concentrations is described using the inventive method.

For this purpose, an overnight culture of the bacterial strain Escherichia coli C600 (PTC Phage Technology Center GmbH) was first prepared under standard conditions at 37° C. in 10 ml TSB (Tryptic Soy Broth) (Sigma-Aldrich). The overnight culture was diluted the following day (1:10 in TSB) and incubated at 37° C. for another two hours. A dilution series was then prepared from the obtained culture by serial dilution with TSB. For determining the bacterial concentration in the serially diluted bacterial suspensions, the optical density was measured at 600 nm ($OD_{600}$). FIG. 12 A shows the data of the bacterial titre for the different dilution stages.

The initial fluorescence intensity in the phage suspension prior to the addition of a sample to be tested was determined by mixing 900 µl of a suspension of 5(6)-carboxyfluorescin-labelled TB54 bacteriophages and Alexa532-labelled TB99 bacteriophages ($\sim 10^8$ pfu/ml in PBS mixed with 10 mM $MgCl_2$) with 100 µl TSB medium and incubating for 5-10 min at room temperature (RT). The Alexa532-labelled TB99 bacteriophage serves as a reference bacteriophage with disjunct labelling. The fluorescence signals of the test bacteriophage (5(6)-carboxyfluorescin-TB54) and of the reference bacteriophage (Alexa532-TB99) were measured subsequently using a plate reader (Perkin Elmer). The obtained data were defined as the initial intensity or 100% signal intensity of the phage suspension prior to the addition of a sample to be tested, the initial intensity being shown in the graph in FIG. 12 B as a dashed line.

Furthermore, 900 µl of the above suspension were each mixed with 100 µl of the respective serially diluted E. coli C600 bacterial suspension ($\sim 10^4$-$10^7$ cells/ml in TSB) and the reaction mixtures were incubated for 5-10 min at room temperature (RT). The reaction mixtures were then filtered through a filter with a pore size of 0.4 µm (micropore membrane, milipore), respectively.

The fluorescence in the obtained filtrates was measured with a plate reader (Perkin Elmer), respectively. FIG. 12 B shows the fluorescence intensities of unbound 5(6)-carboxyfluorescin-labelled TB54 bacteriophages (shown as squares) and Alexa532-labelled TB99 bacteriophages (shown as triangles) in the filtrate. The indicated fluorescence intensities were each obtained by normalization to the determined value of the initial intensity, i.e. the measured fluorescence intensities were each related to the initial intensity. It can be seen that the fluorescence intensity of the test bacteriophage (5(6)-carboxyfluorescin-TB54 shown as squares) decreases significantly. This demonstrates that the test bacteriophages specifically infect the bacterial strain E. coli C600 and form the corresponding bacteria-bacteriophages-complexes, which are removed by filtration. As a result, the number of unbound test bacteriophages in the filtrate is lower than in the initial phage suspension, which is reflected in the decrease in fluorescence intensity in the filtrate.

The fluorescence intensities in the retentate are shown in FIG. 12 C. The indicated data were each determined fluorescence microscopically by photocopying the filter surfaces with a standard objective lens (20×, Nikon) and calculating the average image intensity from three images per filter surface (mean value±standard deviation, N=3). The data show that the fluorescence intensity of the test bacteriophage (5(6)-carboxyfluorescin-TB54) increases together with the increase in the bacterial concentration in the added sample, whereas the fluorescence intensity of the reference bacteriophage (Alexa532-TB99) hardly changes. It can hence be concluded that the test bacteriophage specifically binds to the bacteria to be detected and that the concentration of the formed bacteria-bacteriophages-complexes, which are finally immobilized on the filter surface by filtration, increases as the concentration of bacteria increases. In contrast, the reference bacteriophage does not bind to the bacterial species or strain to be detected, so that the concentration of the bacteria has no influence on the fluorescence intensity measured for the reference bacteriophage in the retentate.

As demonstrated, the inventive method allows a highly specific and highly sensitive detection of bacteria. The method is easy to carry out and provides very reliable results. In addition, the time required for the procedure is low, so that detection is enabled within less than one hour as of the addition of a sample.

The invention claimed is:

1. A method for the detection of bacteria comprising the steps of
   A) provision of one or more suspensions each comprising at least one species of labelled test bacteriophages which specifically bind to a bacterial species to be detected;
   B) addition of a sample to be tested for the presence of at least one bacterial species to be detected to the one or more suspensions;
   C) filtration of the resulting reaction mixture, wherein a filter with a pore size of 0.1 μm to 0.5 μm is used;
   D) detection of bacteria-bacteriophages-complexes in the retentate, provided that at least one bacterial species to be detected is present, wherein the complexes consist of bacteria of the at least one bacterial species to be detected and test bacteriophages of the at least one species of test bacteriophages bound thereto;
   E) detection of unbound test bacteriophages in the filtrate;
   F) processor-aided processing of received signals generated by the detection in steps D) and E) and output of detection results to a user,
   wherein the one or more suspensions further comprise a labelled reference bacteriophage which does not bind to any bacterial species to be detected and which has a label disjunct from the test bacteriophages such that labelled reference bacteriophage is also detected in step E); or wherein labelled microparticles or nanoparticles are used in alternative to a labelled reference bacteriophage, which do not bind to any bacterial species to be detected and can pass through the filter due to their small size.

2. The method for the detection of bacteria according to claim 1, wherein the bacterial species to be detected are selected from the group comprising *Staphylococcus aureus*, Methicillin-resistant *Staphylococcus aureus* (MRSA), *Staphylococcus epidermidis*, *Streptococcus pneumoniae*, *Streptococcus pyogenes*, *Haemophilus influenzae*, *Haemophilus parainfluenzae*, *Klebsiella pneumoniae*, *Escherichia coli*, *Escherichia hermannii*, EHEC, *Enterobacter cloacae*, *Enterococcus faecalis*, *Enterococcus faecum*, *Pseudomonas aeruginosa*, *Proteus mirabilis*, *Proteus vulgaris*, *Staphylococcus saprophyticus*, *Bacteroides fragilis*, *Enterococcus faecium*, *Enterobacter aerogenes*, *Serratia marcescens*, B-*Streptococcus* (agalactiae), *Chlamydia trachomatis*, *Chlamydia psittaci*, *Ureaplasma urealyticum*, *Mycoplasma hominis*, *Mycoplasma pneumoniae*, *Neisseria gonorrhoeae*, *Neisseria meningitidis*, *Citrobacter freundii*, *Moraxella catarrhalis*, *Stenotrophomonas maltophilia*, *Pasteurella multocida*, *Acinetobacter baumannii*, *Providencia rettgeri*, *Bordetella pertussis*, *Bacillus anthracis*, *Bacillus cereus*, *Brucella abortus*, *Brucella melitensis*, *Clostridium butolinum*, *Clostridium difficile*, *Clostridium tetani*, *Clostridium perfringens*, *Clamydia trachomatis*, *Corynebacterium diphtheriae*, *Francisella tularensis*, *Gardenella vaginalis*, *Listeria monocytogenes*, *Morganella morganii*, *Mycobacterium leprae*, *Mycobacterium tuberculosis*, *Nocardia asteriodes*, *Salmonella bongori*, *Salmonella enterica*, *Shigella* spp., *Vibrio cholerae*, *Borrelia burgdorferi*, *Yersinia pestis*, *Yersinia enterocolitica*, *Coxiella bumettii*, *Aeromonas* spp., *Plesiomonas* spp., *Xanthomonas maltophilia*, *Treponema pallidum*, *Eikenella corrodens*, *Spirillum minus*, *Rickettsia prowazeki*, *Rickettsia rickettsii*, *Rickettsia conorii*, *Cronobacter* spp., *Campylobacter* spp. and *Legionella pneumophilia*.

3. The method for the detection of bacteria according to claim 1, wherein the one or more suspensions each comprise two or more species of labeled test bacteriophages which each specifically bind to different bacterial species to be detected and wherein the labels of the species are disjunct or partially overlapping and wherein the label is characteristic of the respective species of test bacteriophages.

4. The method for the detection of bacteria according to claim 1, wherein the label comprises at least one reporter molecule having fluorescent or chemiluminescent properties or at least one reporter molecule which emits light by interaction with a secondary molecule.

5. The method for the detection of bacteria according to claim 4, wherein the label consists of at least one fluorescent reporter molecule, respectively, and the detection is carried out by measuring the fluorescence, wherein the excitation of at least one fluorescent reporter molecule is carried out in the wavelength range of from 200-1000 nm.

6. The method for the detection of bacteria according to claim 4, wherein the at least one reporter molecule is coupled to proteins in the capsid region of the bacteriophages.

7. Method for the detection of bacteria according to claim 4, wherein the detection is carried out by time-resolved measurement of the light emission.

8. The method for the detection of bacteria according to claim 1, further comprising a step G) of mixing the sample with the one or more suspensions and incubating the resulting reaction mixture, wherein step G) follows step B).

9. The method for the detection of bacteria according to claim 1, further comprising the step of a pre-separation of bacteria-bacteriophages-complexes and unbound bacteriophages, wherein the pre-separation follows step B).

10. A reaction vessel for the detection of bacteria,
   comprising at least two compartments separated from each other by a filter,
      wherein the filter has a pore size of 0.1 μm to 0.5 μm
         wherein one compartment is a phage reservoir containing a suspension which comprises at least one species of labeled test bacteriophages that specifically bind to a bacterial species to be detected, and
      one compartment is a collection reservoir for receiving the filtrate after the addition of a sample to the suspension and filtration through the filter;
   a means for identifying the reaction vessel; and
   at least two measurement windows, wherein one measurement window is arranged in the region of the filter surface facing the phage reservoir, and one measuring window is arranged in the region of the collection reservoir, wherein the suspension further comprises a labelled reference bacteriophage which does not bind to any bacterial species to be detected and which has a label disjunct from the test bacteriophages; or wherein the reaction vessel comprises a further compartment, which contains an indicator solution with labeled microparticles that do not bind to any bacterial species to be detected and that may pass through the filter due to their small size.

11. The reaction vessel according to claim 10, wherein the suspension comprises two or more species of labeled test bacteriophages which each specifically bind to different bacterial species to be detected and wherein the labels of the species are disjunct or partially overlapping and wherein the label is characteristic of the respective species of test bacteriophages.

12. The reaction vessel according to claim 10, further comprising a compartment between the phage reservoir and the filter, which contains at least one pre-filter.

13. A cartridge, comprising
two or more reaction vessels according to claim 10, which are arranged parallel and/or in series to each other,
wherein each parallel reaction vessel contains different species of labeled test bacteriophages in the suspension of the phage reservoir, each specifically binding to different bacterial species to be detected.

14. The cartridge according to claim 13, wherein the labels of the different species of labeled test bacteriophages are disjunct or partially overlapping.

15. A measuring device for the detection of bacteria, comprising
a slot into which a reaction vessel according to claim 10 is inserted;
at least two detection optics, each of which is arranged in the region of the measuring windows of the inserted reaction vessel,
wherein the detection optics each comprise a lens system for focusing light emitted by the label of the bacteriophages onto at least one sensor, the at least one sensor detecting the emitted light;
a processor which is connected to the at least one sensor of the detection optics, respectively, and which processes the received detection signals; and
an output unit connected to the processor, which outputs the detection results to a user.

16. The measuring device according to claim 15, wherein the detection optics further each comprise an illumination unit, which emits light in the wavelength range of from 200-1000 nm, and a lens system for focusing the light emitted by the illumination unit onto a measuring area, wherein the illumination unit is also connected to and controlled by the processor.

17. The measuring device according to claim 15, further comprising an integrated reader that detects the means for identifying the reaction vessel and forwards the detected data to the processor, whereby the processor processes the detected data and outputs the results of the identification to a user via the output unit.

18. The measuring device according to claim 15, wherein the at least one sensor comprises one or more optical sensors and/or one or more spectral photometers, optionally equipped with an emission filter.

19. A measuring device for the detection of bacteria, comprising
a slot into which a cartridge according to claim 13 is inserted;
at least two detection optics, each of which is arranged in the region of the measuring windows of the inserted reaction vessel or cartridge,
wherein the detection optics each comprise a lens system for focusing light emitted by the label of the bacteriophages onto at least one sensor, the at least one sensor detecting the emitted light;
a processor which is connected to the at least one sensor of the detection optics, respectively,
and which processes the received detection signals; and
an output unit connected to the processor, which outputs the detection results to a user.

20. The measuring device according to claim 19, wherein the detection optics further each comprise an illumination unit, which emits light in the wavelength range of from 200-1000 nm, and a lens system for focusing the light emitted by the illumination unit onto a measuring area, wherein the illumination unit is also connected to and controlled by the processor.

21. The measuring device according to claim 19, further comprising an integrated reader that detects the means for identifying the reaction vessel and forwards the detected data to the processor, whereby the processor processes the detected data and outputs the results of the identification to a user via the output unit.

22. The measuring device according to claim 19, wherein the at least one sensor comprises one or more optical sensors and/or one or more spectral photometers, optionally equipped with an emission filter.

\* \* \* \* \*

UNITED STATES PATENT AND TRADEMARK OFFICE
CERTIFICATE OF CORRECTION

PATENT NO.         : 10,766,030 B2
APPLICATION NO.    : 15/777662
DATED              : September 8, 2020
INVENTOR(S)        : Walter Miedl et al.

Page 1 of 1

It is certified that error appears in the above-identified patent and that said Letters Patent is hereby corrected as shown below:

In the Claims

In Claim 1, at Line 2, insert a --:-- after "steps of";
    At Line 8, change the second occurrence of "to" to "in"; and
    At Line 26, insert --the-- before "labelled reference".

In Claim 10, at Line 4, insert a --,-- at the end of the line.

In Claim 13, at Line 1, insert a --:-- after "comprising"; and
    At Line 2, insert a --,-- after "vessels".

In Claim 15, at Line 2, insert a --:-- after "comprising".

In Claim 16, at Line 2, change "each comprise" to "each comprises".

In Claim 19, at Line 2, insert a --:-- after "comprising"; and
    At Line 6, change "each comprise" to "each comprises".

In Claim 20, at Line 2, change "each comprise" to "each comprises".

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*